(12) United States Patent
Zhao et al.

(10) Patent No.: US 7,583,379 B2
(45) Date of Patent: Sep. 1, 2009

(54) SURFACE ENHANCED RAMAN SPECTROSCOPY (SERS) SYSTEMS AND METHODS OF USE THEREOF

(75) Inventors: Yiping Zhao, Statham, GA (US);
Richard A. Dluhy, Athens, GA (US);
Ralph A. Tripp, Watkinsville, GA (US);
Stephen Chaney, Athens, GA (US);
Sarat Shanmukh, Athens, GA (US);
Leslie P. Jones, Watkinsville, GA (US)

(73) Assignee: University of Georgia Research Foundation, Athens, GA (US)

( * ) Notice: Subject to any disclaimer, the term of this patent is extended or adjusted under 35 U.S.C. 154(b) by 412 days.

(21) Appl. No.: 11/495,980

(22) Filed: Jul. 28, 2006

(65) Prior Publication Data

US 2009/0149344 A1 Jun. 11, 2009

Related U.S. Application Data

(60) Provisional application No. 60/703,110, filed on Jul. 28, 2005.

(51) Int. Cl.
*G01J 3/44* (2006.01)
(52) U.S. Cl. .................. 356/301; 436/164; 436/171; 435/6
(58) Field of Classification Search .................. 356/301; 435/6, 7.2; 436/164, 171
See application file for complete search history.

(56) References Cited

U.S. PATENT DOCUMENTS

| | | | |
|---|---|---|---|
| 4,874,664 A | 10/1989 | Hamaguchi | |
| 5,780,232 A | 7/1998 | Arlinghaus | |
| 5,821,060 A | 10/1998 | Arlinghaus | |
| 5,864,397 A | 1/1999 | Vo-Dinh | |
| 5,866,204 A | 2/1999 | Robbie | |
| 6,002,471 A | 12/1999 | Quake | |

(Continued)

FOREIGN PATENT DOCUMENTS

EP 0 261 642 9/1987

(Continued)

OTHER PUBLICATIONS

Vaeth, et al.; Transition Metals for Selective Chemical Vapor Deposition of Parylene-Based Polymers; Apr. 18, 2000; Chem. Mater, 2000, 12, pp. 1305-1313.

(Continued)

*Primary Examiner*—L. G Lauchman
(74) *Attorney, Agent, or Firm*—Thomas, Kayden, Horstemeyer & Risley, LLP

(57) ABSTRACT

Surface-enhanced Raman spectroscopic (SERS) systems and methods for detecting biomolecules of interest, such as a virus, bacterium, or other infectious agent, are provided. A spectroscopic assay based on surface enhanced Raman scattering (SERS) using a silver nanorod array substrate fabricated by oblique angle deposition has been developed that allows for rapid detection of trace levels of viruses or bacteria with a high degree of sensitivity and specificity. This novel and improved SERS assay can detect minor spectral differences within strains of a single virus type such as respiratory syncytial virus or influenza virus in the presence of biological media. The method provides rapid diagnostics for direct molecular and structural characterization of virus strains and virus gene deletion mutants generating reproducible viral spectra without viral manipulation.

29 Claims, 19 Drawing Sheets

U.S. PATENT DOCUMENTS

| | | | |
|---|---|---|---|
| 6,081,328 | A | 6/2000 | Eng |
| 6,149,868 | A | 11/2000 | Natan et al. |
| 6,174,677 | B1 | 1/2001 | Vo-Dinh |
| 6,180,415 | B1 | 1/2001 | Schultz et al. .............. 436/518 |
| 6,206,065 | B1 | 3/2001 | Robbie |
| 6,219,137 | B1 | 4/2001 | Vo-Dinh |
| 6,242,264 | B1 | 6/2001 | Natan |
| 6,248,422 | B1 | 6/2001 | Robbie |
| 6,376,177 | B1 | 4/2002 | Poponin ........................ 435/6 |
| 6,406,777 | B1 | 6/2002 | Boss |
| 6,514,767 | B1 | 2/2003 | Natan |
| 6,608,716 | B1 | 8/2003 | Armstrong |
| 6,614,523 | B1 | 9/2003 | Boss |
| 6,623,977 | B1 | 9/2003 | Farquharson |
| 6,624,886 | B2 | 9/2003 | Natan |
| 6,649,683 | B2 | 11/2003 | Bell |
| 6,699,724 | B1 | 3/2004 | West |
| 6,750,065 | B1 | 6/2004 | White |
| 6,770,488 | B1 | 8/2004 | Carron |
| 6,778,316 | B2 | 8/2004 | Halas |
| 6,781,690 | B2 | 8/2004 | Armstrong |
| 6,838,121 | B2 | 1/2005 | Weimer |
| 7,192,703 | B2 | 3/2007 | Sun et al. |
| 7,267,948 | B2 | 9/2007 | Vo-Dinh |
| 7,361,313 | B2 | 4/2008 | Chan et al. |
| 7,397,558 | B2 | 7/2008 | Kamins et al. |
| 7,400,395 | B2 | 9/2008 | Chan et al. |
| 2002/0106648 | A1 | 8/2002 | Lizardi |
| 2002/0123050 | A1 | 9/2002 | Poponin |
| 2002/0182716 | A1 | 12/2002 | Weisbuch |
| 2003/0029274 | A1 | 2/2003 | Natan |
| 2003/0059820 | A1 | 3/2003 | Vo-Dinh |
| 2003/0073139 | A1 | 4/2003 | Kreimer |
| 2003/0124595 | A1 | 7/2003 | Lizardi |
| 2003/0128428 | A1 | 7/2003 | Anderson |
| 2003/0157732 | A1 | 8/2003 | Baker |
| 2003/0166297 | A1 | 9/2003 | Natan |
| 2003/0186240 | A1 | 10/2003 | Su |
| 2003/0187237 | A1 | 10/2003 | Chan |
| 2003/0231304 | A1 | 12/2003 | Chan |
| 2004/0023046 | A1 | 2/2004 | Schlottig |
| 2004/0053222 | A1 | 3/2004 | Storhoff |
| 2004/0086897 | A1 | 5/2004 | Mirkin |
| 2004/0096981 | A1 | 5/2004 | Weimer |
| 2004/0110208 | A1 | 6/2004 | Chan |
| 2004/0126790 | A1 | 7/2004 | Su |
| 2004/0135997 | A1 | 7/2004 | Chan |
| 2004/0180379 | A1 | 9/2004 | Van Duyne |
| 2004/0219221 | A1 | 11/2004 | Moore |
| 2004/0224321 | A1 | 11/2004 | Nicolau et al. |
| 2005/0003376 | A1 | 1/2005 | Kneipp |
| 2005/0019784 | A1 | 1/2005 | Su |
| 2005/0037514 | A1 | 2/2005 | Carron |
| 2005/0048651 | A1 | 3/2005 | Ryttsen |
| 2005/0053966 | A1 | 3/2005 | Poponin |
| 2005/0074779 | A1 | 4/2005 | Vo-Dinh |
| 2005/0084980 | A1 | 4/2005 | Koo |
| 2006/0147927 | A1 | 7/2006 | Geddes et al. |
| 2006/0246460 | A1 | 11/2006 | Graham et al. |
| 2006/0252065 | A1* | 11/2006 | Zhao et al. ...................... 435/6 |
| 2007/0165209 | A1* | 7/2007 | Natan et al. ................... 356/71 |
| 2007/0188749 | A1* | 8/2007 | Brady et al. ................. 356/301 |
| 2008/0059135 | A1 | 3/2008 | Murugkar et al. |
| 2008/0096005 | A1* | 4/2008 | Premasiri .................... 428/323 |

FOREIGN PATENT DOCUMENTS

| | | |
|---|---|---|
| WO | WO01/71353 | 9/2001 |
| WO | WO03/095973 | 11/2003 |
| WO | WO03/106943 | 12/2003 |
| WO | WO2004/004647 | 1/2004 |
| WO | 2004059279 | 7/2004 |
| WO | WO2004/074790 | 9/2004 |
| WO | WO2004/085988 | 10/2004 |
| WO | WO2005/019812 | 3/2005 |
| WO | WO 2006/005111 | 7/2005 |
| WO | WO 2006/066180 | 12/2005 |
| WO | 2006/137885 | 12/2006 |
| WO | 2007059514 | 5/2007 |
| WO | WO 2007/135593 A1 | 11/2007 |
| WO | 2008045114 | 4/2008 |

OTHER PUBLICATIONS

Vaeth, et al.; Use of Microcontact Printing for Generating Selectively Grown Films of Poly (p-phenylen vinylene) and Parylenes Prepared by Chemical Vapor Deposition; Sep. 22, 2000; Langmuir 2000, 16, pp. 8495-8500.

Pursel, et al.; Growth of Sculptured Polymer Submicronwire Assembles by Vapor Deposition; 2005; Polymer 46 (2005) pp. 95544-9548.

Hu, et al.; Fabrication, Characterization, and Application in SERS of Self-Assembled Polyelectrolyte-Gold Nanorod Multilayered Films; Sep. 22, 2005; J. Phys. Chem. B 2005, 109, pp. 19385-19389.

Guo, et al.; Bifunctional Au @pt Hybrid Nanorods; 2007; Journal of Colloid and Interface Science, 315 (2007) pp. 363-368.

Suzuki, e tal.; Au Nanorod Arrays Tailored for Surface-Enchanced Raman Spectroscopy; 2007; Analytical Sciences; Jul. 2007, vol. 23; pp. 829-833.

Suzuki, et al.; In-Line Aligned and Bottom-Up Ag Nanorods for Surface-Enhanced Raman Spectroscopy; 2006; Applied Physics Letters; 88, 2003121 (2006); 3 pages.

Tiwari, et al.; Non-Resonance SERS Effects of Silver Colloids with Different Shapes; 2007; Chemical Physics Letters, 446 (2007) pp. 77-82.

Chu, et al.; A High Sensitive Fiber SERS Probe Based on Silver Nanorod Arrays; Optics Express; vol. 15, No. 19; Sep. 17, 207; pp. 12230-12239.

Chu, et al.; Silver Nanorod Arrays as a Surface-Enhanced Raman Scattering Substrate for Foodborne Pathogenic Bacteria Detection; 2008; Applied Spectroscopy, vol. 62, No. 8, 2008; pp. 922-931.

Yao, et al.; Cobalt and Nickel Nanorod Array Electrodes as New SERS Active Substrates; 2007; 2 pages.

Yang, et al.; Aligned Silver nanorod Arrays for Surface-Enhanced Rman Scattering; 2006; on-line at www.iop.org/EJ/abstract/0957-4484/17/10/038.

Zhao, et al.; Aligned Copper nanorod Arrays for Surface-enhanced Raman Scattering; 2007; online at http://ieeexplore.ieee.org/Xplore/dfdeny.jsp?url=/ie15/4295685/429 . . . .

Wang, et al.; Layer uniformity of glancing angle deposition; Vaccum; vol. 78, Issue 1, Apr. 4, 2005, pp. 107-111.

Schubert, et al.; Nanostructure fabrication by glancaing angle ion beam assisted deposition of silicon; Applied Physics A: Materials Science & Processing; vol. 81, No. 3 / Aug. 2005.

Brett et al.; Glancing Angle Deposition, An Overview of Thin Films and GLAD; http://www.ece.ualberta.ca/~glad/glad.html; 2006.

Gish, et al.; Evaluation of silver nanostructures fabricated using glancing angle deposition as localized surface plasmon resonance biosensors; nanotech 2007 Conference Program Abstract.

Zhao, et al.; Designing Nanostructures by Glancing Angle Deposition; Proceedings of SPIE; vol. 5219; Nanotubes and Nanowires; Invited Paper, pp. 59-73.

Katherine A. Willets and -Richard P. Van Duyne; Localized Surface Plasmon Resonance Spectroscopy and Sensing; Annual Review of Physical Chemistry; vol. 58: 267-297 (Volume publication date May 2007); First published online as a Review in Advance on Oct. 26, 2006.

ARS Project: 408043—Annual Reports for 2004-2007; USDA Agricultural Research Service.

Big Discovery Symposium 2006; UC Santa Barbara; Epigenetic Enzymes and Therapies; slide show.

Kathy Kincade; Raman Spectroscopy: SERS and Silver Nanorods Quickly Reveal Viral Structures; Laser Focus World; Jan. 1, 2007.

Kathy Kincade; Optoelectronic Applications: Nanophotonics—An "Old" Technique Finds New Life in the Nano World; Laser Focus World; Oct. 1, 2006.

Kawai, et al.; Raman Spectroscopic Probes Withstand Hostile Environments; Laser Focus World; Jun. 1, 2005.

Amri, et al.; Adenine and RNA in Mineral Samples. Surface-Enchaned Raman Spectroscopy (SERS) for Picomole Detections; Spectrochimica Acta Part A 59 (2003) pp. 2645-2654.

Stuart, et al.; In Vivo Glucose Measurement by Surface-Enhanced Raman Spectroscopy; Anal. Chem. 2006, 78, pp. 7211-7215.

Faulds, et al.; DNA Detection by Surface Enchanced Resonance Raman Scattering (SERRS); The Royal Society of Chemistry 2005; Analyst, 2005, 130, pp. 1125-1131.

Bell, et al.; Surface-Enhanced Raman Spectroscopy (SERS) for Sub-Micromolar Detection of a DNA/RNA Mononucleotides; J. Am. Chem. Soc. 2006, 128, pp. 15580-15581.

Yun Wei Charles Cao, et al.; Nanoparticles with Raman Spectroscopic Fingerprints for DNA and RNA Detection; Science, 297; 2002; pp. 1536-1540.

Mecham, et al.; Research on Bettering Surveillance of Arboviral Threats, Using West Nile Virus as a Model; USDA Agricultural Research Service; abstract.

Gish, et al.; Evaluation of Silver nanostructures Fabricated Using Glancing Angle Deposition as Localized Surface Plasmon Resonance Biosensors; The Nanotechnology Conference and Trade Show; Boston, Jun. 1-5, 2005; abstract.

Wang, et al.; Layer Uniformity of Glancing Angle Depostion; Vaccum; 78; 2005; pp. 107-111.

Schubert; Nanostructure Fabrication by Blancing Angle Ion Beam Assisted Deposition of Silicon; Appl. Physc. A81, 481-486 (2005).

Willets, et al.; Localized Surface Plasmon Resonance Spectroscopy and Sensing; Annu. Rev. Phys. Chem 2007; 52; 267-297.

Prokes, et al.; Enhanced Plasmon Coupling in Crossed Dielectric/Metal Nanowire Composite Geometries and Applications to Surface-Enhanced Raman Spectroscopy; Appl. Physc. Lett; 90; 2007; 3 pages.

D. Keith Roper; Determining Surface Plasmon Resonance Response Factors for Deposition onto Three-Dimensional Surface; Chemical Engineering Science; 62; 2007; pp. 1988-1996.

Takemoto, et al.; A Surface Plasmon Resonance Assay for the Binding of Influenza Virus Hemagglutinin to Its Sialic Acid Receptor; Virology; 217; 452-458 (1996) Article No.: 0139.

Hardy, et al.; Valency of Antibody Binding to Enveloped Virus Particles as Determined by Surface Plasmon Resonance; Journal of Virology; Jan. 2003; p. 1649-1652; vol. 77, No. 2.

A Graded Improvement; Science, vol. 319; Feb. 29, 2008, p. 1163.

Kim; et al.; Light-Extraction Enhancement of GaInN Light-Emitting Diodes by Graded-Refractive-Index Indium Tin Oxide Anti-Reflection Contact; Adv. Mater. 2008, 20, pp. 801-804.

Robbie, et al.; Sculptured Thin Films and Glancing Angle Deposition: Growth Mechanics and Applications; J. Va. Sci. Technol. A 15(3), May/Jun. 1997; pp. 1460-1465.

Robbie, et al.; Fabrication of Thin Films With Highly Porous Microstructures; J. Va. Sci. Technol. A 13(3), May/Jun. 1995; pp. 1032-1035.

Robbie, et al.; First Thin Film Realization of a Helicoidal Bianisotropic Medium; J. Vac. Sc. Technol. A 13(6), Nov./Dec. 1995; pp. 2991-2993.

Bentley: "Microsensors: Invisible Watchdogs to Keep Us Safe and Well"; http://www.solve.csiro.au/0805/article1.htm; Aug. 2005; 4 pages.

Campion, et al.; "Surface-enhanced Raman scattering"; Chemical Society Reviews, vol. 27; 1998; 10 pages.

Carillo; "Sers nanoparticles: a new optical detection modality for rapid tests"; http://www.cli-online.com/en/featured-articles/sers-nanoparticles-a-new-optical-detection-modality-for-rapid-tests/trackback/1/index.html; Copyright 2004-2007; 4 pages.

Clin; "Applications of nanobiotechnology in Clinical Diagnostics"; http://www.clinchem.org/cgi/content/full/53/11/2002; 2007; 1 page.

Driskell, et al.; "Low-Level Detection of Viral Pathogens by a Surface-Enhanced Raman Scattering Based Immunoassay"; 2005; 8 pages.

Fischer, et al.; "Heightened sense for sensing: recent advances in pathogen immunoassay sensing platforms"; Lawrence Livermore National Laboratory; Feb. 6, 2007; 13 pages.

Goeller, et al.; "Discrimination of Bacteria and Bacteriophages by Raman Spectroscopy and Surface-Enhances Raman Spectroscopy"; Society for Applied Spectroscopy; vol. 61; Nov. 7, 2007; 7 page.

Gordon, et al.; "Plasmonic Sensors Based on Nano-Holes: Technology and Integration"; Micro and Nanotechnologies for Space, Defense, and Security II; vol. 6959; 2008; 6 pages.

Grabar, et al.; "Preparation and Characterization of Au Collolid Monolayers"; The Pennsylvania State University; vol. 67 Feb. 15, 1995; 9 pages.

Grow, et al.; "Evaluation of the Doodlebug: A Biochip for Detecting Waterborne Pathogens"; http://www.iwapublishing.com/template.cfm?name=isbn1843396688; Jun. 1, 2003; 1 page.

Grow, et al.; "New biochip technology for label-free detection of pahogens and their toxins"; Biopraxis, Inc.; Journal of Microbiological Methods; 2003; 13 pages.

Gu, et al.; "Biofunctional magnetic nanoparticles for protein separation and pathogen detection"; ChemComm; Jan. 19, 2006; 9 pages.

Hou, et al.; "Rapid Chip-Scale Detection by Micro-Spiral Flow and Surface Enhanced Raman Scattering"; http://aiche.confex.com/aiche/2006/techprogram/P66060.HTM; Nov. 15, 2006; 2 pages.

Kao, et al.; "Surface-Hanced Raman Detection on Metalized Nanostructured Poly(p-xylylene) Films"; Advanced Materials; 2008; 4 pages.

Koo, et al.; "Single-Molecule detection of biomolecules by surface-enhanced coherent anti-Stokes Raman scattering"; Optics Letters; vol. 30; May 1, 2005; 3 pages.

Richards; "Nano-optics: Imaging beyond the Diffraction Limit, Fluorescence and Lifetime Modification, Surface Enhanced Raman Scattering"; http://www.opticalproteomics.org/research/nanooptics.php#sers; 2 pages.

Service; "Fast, Sensitive Scan Targets Anthrax"; http://www.sciencemag.org/cgi/content/full/308/5718/45?ck=nck; vol. 308; Apr. 1, 2005; 5 pages.

Stokes, et al.; "Detection of E. coli using a microfludics-based antibody biochip detection system"; Advanced monitoring Development Group; Nov. 13, 2000; 7 pages.

Taurozzi; "Sers-Active Silver Nanoparticle Arrays on Track Etch Membrane Support as Flow-through Water Quality Sensors"; http://aiche.confex.com/aiche/2006/techprogram/P59895.HTM; Nov. 15, 2006; 3 pages.

Tay; "Applications of Enhanced Raman Spectroscopy i Biological Sciences"; Institute for Microstructural Sciences; 2005; 12 pages.

Vo-Dinh; "Biosensors, Nanosensors and Biochips: Frontiers in Environmental and Medical Diagnostics"; Oak Ridge National Laboratory; The 1st International Symposium on Micro & Nano Technology; Mar. 2004; 6 pages.

Vo-Dinh, et al.; "Surface-enhanced Raman Scattering (SERS) Method and Instrumentation for Genomics and Biomedical Analysis"; Journal of Raman Spectrosopy; 1999; 9 pages.

Vo-Dinh, et al., "Cancer gene detection using surface-enhanced Raman scattering (SERS)"; Journal of Raman Spectroscopy; Mar. 13, 2002; 6 pages.

Yakes, et al.; "Detection of Mycobacterium avium subsp. paratuberculosis by a Sonicate Immunoassay Based on Surface-Enhanced Raman Scattering"; Clinical and Vaccine Immunology; vol. 15; Feb. 2008; 8 pages.

Tao, A, et al., *Langmuir-Blodgett Silver Nanowire Monolayers for Molecular Sensing Surface-Enhanced Raman Spectroscopy*, Nano Letters 2003, vol. 3, No. 9, 1229-1233.

Nikoobakht, B. et al., *Surface-Enhanced Raman Scattering Studies on Aggregated Gold Nanorod*, J. Phys. Chem A 2003, 107, 3372-3378.

Leverette, C., et al., *Development of A Novel Dual-Layer Thick Ag Substrate for Surface-enhanced Raman Scattering (SERS) of Self-Assmebled Monolayers*, J. Phys. Chem. B 2002, 106, 8747-8755.

Vo-Dinh, *Surface-enhanced Raman Spectroscopy Using Metallic Nanostructures*, Trends in Analytical Chemistry, vol. 17, Nos. 8+9, 1998.

Kneipp, K., *Surface-enhanced Raman scattering and biophysics*, J. Phys. Condens. Matter 14 (2002) R597-R624.

EIC Laboratories, *Application Summary Buried Landmine Detection with SERS*.

Sylvia, J., et al., *Surface-Enhanced Raman Detection of 2,4-Dinitrotoluene Impurity Vapor as a Marker To Locate Landmines*, Anal. Chem. 2000, 72, 5834-5840.

Yang, et al., *A Surface-Enhanced Hyper-Raman and Surface-Enhanced Raman Scattering Study of Trans-1,2-bix(4-pyridy)ethylene Adsorbed Onto Silver Film Over Nanosphere Electrodes, Vibrational assignments: Experimental and Theory*, J. Chem. Phys. 104(11), 4313-4323.

Zeman, E.J., et al., *A Surface Enhanced Resonance Raman Study of Cobalt Phthalocyanine on Rough Ag Films: Theory and Experiment*, J. Chem. Phys. 87(7), 4189-4200.

Norrod, K., *Quantitative Comparison of Five SERS Substrates: Sensitivity and Limit Detection*, Applied Spectroscopy, 1997. 51(7) 994-1001.

Xu, S., et al., *Immunoassay Using Probe-labelling Immunogold Nanoparticles with Silver Staining Enhancement Via Surface-Enhanced Raman Scattering*, The Royal Society of Chemistry, Analyst 2004, 129, 63-68.

Aizpurua, et al; "Optical Properties of Coupled Metallic Nanorods for Field-enhanced Spectroscopy"; The American Physical Society; 2005; 13 pages.

Chaney, et al; "Aligned Silver Nanorod Arrays Produce High Sensitivity Surface-enhanced Raman Spectroscopy Substrates"; American Institute of Physics; 2005; 3 pages.

Coldiron, et al; "Nanotechnology in Cancer"; http://www.concana.com/Nanotechnology.htm; Copyright 2007-2008; 5 pages.

Faulds, et al; "Evaluation of Surface-enhanced Resonance Raman Scattering For Quantitative DNA Analysis"; http://www.nano-biology.net/showabstract.php?pmid=14719891; 2004; 1 page.

Gu, et al; "Optimum Length of Silver Nanorod for Fabrication of Hot Spots"; American Chemical Society; 2007; 4 pages.

Hafner; "Plasmonics: Gold Nanoparticles are Shaped for Effect"; http://www.laserfocusworld.com/articles/article_display.html?id=252462; 2006; 4 pages.

Kim; "Surface Plasmon Resonances of Noble Metal Nanorods and Nanoparticles"; Sungkyunkwan University; May 29, 2007; 29 pages.

Murphy, et al; "Chemical Sensing and Imaging with Metallic Nanorods"; The Royal Society of Chemistry; 2008; 14 pages.

Nikoobakht, et al; "Surface-Enhanced raman Scattering Studies on Aggregated Gold Nanorods"; American Chemical Society; 2003; 7 pages.

Shuyi, et al; "An Approach to Self-Cleaning SERS Sensors by Arraying Au Nanorods on TiO2 Layer"; http://adsabs.harvard.edu/abs/2007SPIE.6647E..13L; 2007; 2 pages.

Suzuki, et al; "Physically Self-Assembled Ag nanorod Arrays for Tunable Plasmonic Sensors"; The Surface Science Society of Japan; 2005; 4 pages.

Suzuki, et al; "Vapor Phase Growth of al Whiskers Induced by Glancing Angle Deposition at High Temperature"; American Institute of Physics; 2006; 3 pages.

Uechi, et al; "Phtochemical and Analytical Applications of Gold Nanoparticles and Nanorods Utilizing Surface Plasmon Resonance"; Anal Bioanal Chem; 2008; 11 pages.

Yao, et al; "A Complementary Study of Surface-enhanced Raman Scattering and Metal Nanorod Arrays"; Pure Appl. Chem, vol. 72; 2000; 8 pages.

Yao, et al; "Electronic Properties of Metal Nanorods Probed by Surface-enhanced Raman Spectroscopy"; Chem. Commun.; The Royal Society of Chemistry; 2000; 2 pages.

* cited by examiner

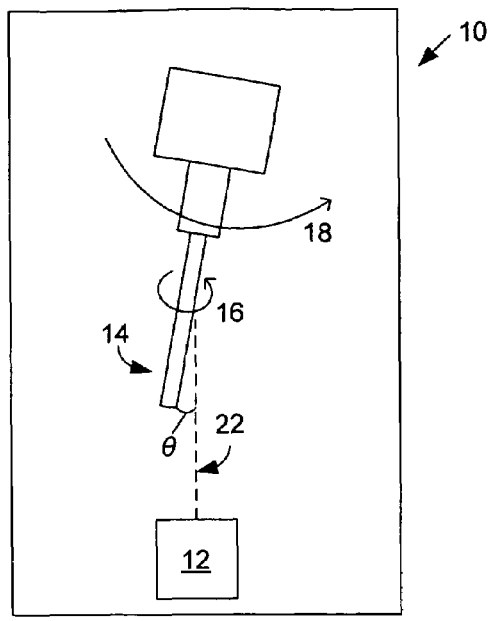
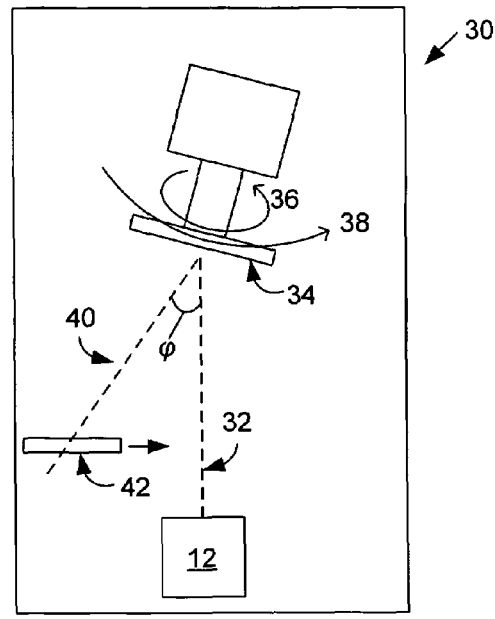
FIG. 1A
FIG. 1B
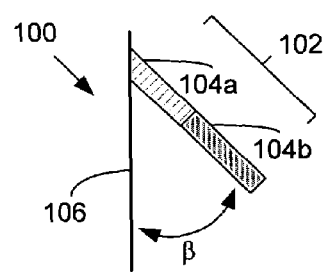
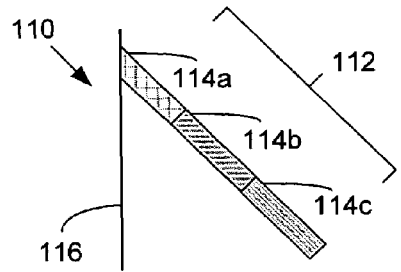
FIG. 2A
FIG. 2B

FIG. 12

*E. Coli* and *S. Aureus* Comparison
*Baseline Corrected Spectra*

SURFACE ENHANCED RAMAN SPECTROSCOPY (SERS) SYSTEMS AND METHODS OF USE THEREOF

CROSS-REFERENCE TO RELATED APPLICATIONS

This application claims priority to co-pending U.S. provisional application entitled "SURFACE ENHANCED RAMAN SPECTROSCOPY (SERS) SYSTEMS, SUBSTRATES, FABRICATION THEREOF, AND METHODS OF USE THEREOF," having Ser. No. 60/703,110, filed Jul. 28, 2005, which is entirely incorporated herein by reference.

This application claims priority to co-pending U.S. patent application entitled, "STRUCTURES HAVING ALIGNED NANORODS AND METHODS OF MAKING," having Ser. No. 11/256,395, filed Oct. 21, 2005, which claims priority to U.S. provisional application entitled, "DIRECT DEPOSITION OF ALIGNED NANOROD ARRAY ONTO CYLINDRICAL OBJECTS," having Ser. No. 60/620,810, filed Oct. 21, 2004, both of which are entirely incorporated herein by reference.

This application claims priority to co-pending U.S. patent application entitled, "SURFACE ENHANCED RAMAN SPECTROSCOPY (SERS) SYSTEMS, SUBSTRATES, FABRICATION THEREOF, AND METHODS OF USE THEREOF" having Ser. No. 11/376,661, filed on Mar. 15, 2006, which claims priority to U.S. provisional application entitled "SURFACE ENHANCED RAMAN SPECTROSCOPY (SERS) SYSTEMS, SUBSTRATES, FABRICATION THEREOF, AND METHODS OF USE THEREOF," having Ser. No. 60/662,089, filed Mar. 15, 2005, both of which are entirely incorporated herein by reference.

STATEMENT REGARDING FEDERALLY SPONSORED RESEARCH OR DEVELOPMENT

Aspects of this disclosure were made with government support under ECS-0304340 awarded by the National Science Foundation and under EB001956 awarded by the National Institutes of Health. The government has certain rights in the invention(s).

FIELD OF THE INVENTION(S)

The present disclosure is generally directed to surface-enhanced Raman spectroscopic (SERS) systems and methods for detection of analytes, in particular, the detection of biomolecules using nanostructures, particularly nanorods. The present disclosure is further directed to SERS systems and methods for detection of a biomolecule of interest, such as a virus or other infectious agent.

BACKGROUND

The discovery of single-molecule and single-nanoparticle surface-enhanced Raman scattering (SERS) has attracted considerable interest, both for fundamental studies of enhancement mechanisms and for potential applications in ultrasensitive optical detection and spectroscopy. A number of researchers have shown that the enhancement factors are as large as $10^{14}$-$10^{15}$, leading to Raman scattering cross sections that are comparable to or even larger than those of fluorescent organic dyes. This enormous enhancement allows spectroscopic detection and identification of single molecules located on the surface of single nanoparticles or at the junction of two particles at room temperature. Progress has been made concerning both the structural and mechanistic aspects of single-molecule SERS, but it is still unclear how this large enhancement effect might be exploited for applications in analytical chemistry, molecular biology, or medical diagnostics. One major problem is the intrinsic interfacial nature of SERS, which requires the molecules to adsorb on roughened metal surfaces. For biological molecules such as peptides, proteins, and nucleic acids, surface-enhanced Raman data are especially difficult to obtain, hard to interpret, and nearly impossible to reproduce. Therefore, a need in the industry exists to improve SERS data for biological molecules.

The current state-of-the-art for viral diagnostic methods involves isolation and cultivation of viruses and may employ (1) an enzyme-linked immunosorbant assay (ELISA), a method that uses antibodies linked to an enzyme whose activity can be used for quantitative determination of the antigen with which it reacts, or (2) polymerase chain reaction (PCR), a method of amplifying fragments of genetic material so that they can be detected. These diagnostic methods are cumbersome, time-consuming, and ELISA has limited sensitivity.

For example, for RSV, isolation of the virus in cell culture has been considered the reference diagnostic method, followed by immunofluorescence assay (IFA) or enzyme immunosorbant assay (EIA). However, results from virus isolation studies are not rapidly available for patient management, and are not sufficiently sensitive to detect infection in a substantial portion of patients. There is, therefore, a critical need for a rapid, reproducible and highly sensitive and specific method of diagnosing viruses such as RSV that inflict substantial disease burdens on human and animal health and (not insignificantly) for other respiratory viruses that also pose a significant threat as agents for bioterrorism. The emergence of biosensing strategies that leverage nanotechnology for direct, rapid, and increased sensitivity in detection of viruses, are needed to bridge the gap between the unacceptably low sensitivity levels of current bioassays and the burgeoning need for more rapid and sensitive detection of infectious agents.

Various bacterial strains are responsible for numerous human diseases. Bacterial infection, such as *Escherichia coli*, is the cause of millions of hospitalizations and thousands of deaths each year. Current detection and diagnostic methods for many bacterial pathogens are not sensitive enough for early and rapid detection. For instance, the infectious dose of a pathogen such as *E. coli* O157:H7 is as low as 10 cells and the existing standard for *E. coli* in water is 4-cells/100 ml, which is far beyond the current detection limit with short detection time. Thus, improved systems and methods for the detection of pathogens and other biomolecules is needed.

SUMMARY

SERS systems and methods for detecting an analyte of interest, particularly a biomolecule of interest are disclosed. Briefly described, a representative embodiment of a method of detecting at least one biomolecule in a sample, among others, includes: attaching at least one first biomolecule to an array of nanorods on a substrate; exposing the substrate including the first biomolecule to the sample containing at least one of a second biomolecule and a third biomolecule; and measuring a surface enhanced Raman spectroscopy (SERS) spectrum, wherein a SERS spectrum of the array of nanorods and the first biomolecule is detectably different than a SERS spectrum of the array of nanorods, the first biomolecule, and the second biomolecule and a SERS spectrum of the array of nanorods, the first biomolecule, and the third biomolecule, and wherein the SERS spectrum of the array of nanorods, the first biomolecule, and the second biomolecule is detectably different than the SERS spectrum of the array of nanorods, the first biomolecule, and the third biomolecule.

Briefly described, a representative embodiment of a method of detecting at least one virus in a sample, among others, includes: exposing a substrate having an array of nanorods on the substrate to the sample including at least one of a first virus and a second virus; and measuring a surface enhanced Raman spectroscopy (SERS) spectrum, wherein a SERS spectrum of the array of nanorods and first virus is detectably different than a SERS spectrum of the array of nanorods and the second virus.

Other aspects, compositions, methods, features, and advantages of the present disclosure will be or become apparent to one with skill in the art upon examination of the following drawings and detailed description. It is intended that all such additional compositions, methods, features, and advantages be included within this description, be within the scope of the present disclosure, and be protected by the accompanying claims.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1 illustrates embodiments of modified oblique angle deposition (OAD) systems for a non-planar substrate (1A) and planar substrate (1B).

FIGS. 2A through 2E illustrate exemplary schematic representations of various combinations and shapes of nanostructures on SERS substrates.

FIG. 12 illustrates a SERS spectra of IgG2a antibody complex (top) and RSV-IgG2a complex (bottom) on an Ag nanorod array made according to an embodiment of the present disclosure.

DETAILED DESCRIPTION

Figure 2C:
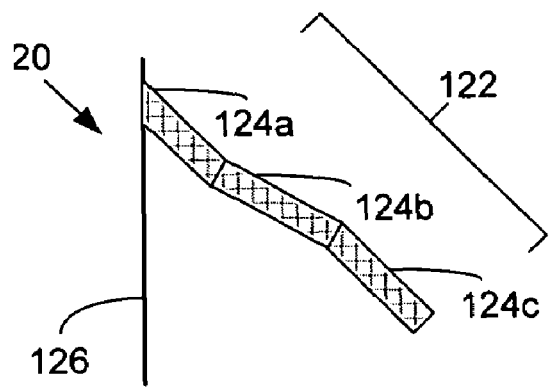

Before the embodiments of the present disclosure are described in detail, it is to be understood that unless otherwise indicated the present disclosure is not limited to particular materials, reagents, reaction materials, manufacturing processes, or the like, as such may vary. It is also to be understood that the terminology used herein is for purposes of describing particular embodiments only, and is not intended to be limiting. It is also possible in the present disclosure that steps may be executed in different sequence where this is logically possible.

It must be noted that, as used in the specification and the appended claims, the singular forms "a," "an" and "the" include plural referents unless the context clearly dictates otherwise. In this specification and in the claims that follow, reference will be made to a number of terms that shall be defined to have the following meanings, unless a contrary intention is apparent.

DEFINITIONS

Use of the phrase "biomolecule" is intended to encompass deoxyribonucleic acid (DNA), ribonucleic acid (RNA), nucleotides, oligonucleotides, nucleosides, proteins, peptides, polypeptides, selenoproteins, antibodies, protein complexes, combinations thereof, and the like. In particular, the biomolecule can include, but is not limited to, naturally occurring substances such as polypeptides, polynucleotides, lipids, fatty acids, glycoproteins, carbohydrates, fatty acids, fatty esters, macromolecular polypeptide complexes, vitamins, co-factors, whole cells, eukaryotic cells, prokaryotic cells, microorganisms such as viruses, bacteria, protozoa, archaea, fungi, algae, spores, apicomplexan, trematodes, nematodes, mycoplasma, or combinations thereof.

In a preferred aspect, the biomolecule is a virus, including, but not limited to, RNA and DNA viruses. In particular the biomolecule is a virus, which may include, but is not limited to, negative-sense and positive-sense RNA viruses and single stranded (ss) and double stranded (ds) DNA viruses. The ds group I DNA viruses include the following families: Adenoviridae, Herpesviridae, Papillomaviridae, Polyomaviridae, Poxyiridae, and Rudiviridae. The group II ssDNA viruses include the following families: Microviridae, Geminiviridae, Circoviridae, Nanoviridae, and Parvoviridae. The ds group III RNA viruses include the following families: Birnaviridae and Reoviridae. The group IV positive-sense ssRNA virus families: Arteriviridae, Coronaviridae, Astroviridae, Caliciviridae, Flaviviridae, Hepeviridae, Picornaviridae, and Togaviridae. The group V negative-sense ssRNA virus families: Bornaviridae, Filoviridae, Paramyxoviridae, Rhabdoviridae, Arenaviridae, Bunyaviridae, and Orthomyxoviridae.

The biomolecule can be one of a number of strands of the virus and/or a mutated version of a virus or of one of a number of strands of a virus.

In a preferred aspect, the biomolecule is bacteria. In particular, the bacteria can include, but is not limited to, Gram-positive or Gram-negative bacteria. The Gram-positive bacteria may include, but is not limited to, Gram positive Cocci (e.g., *Streptococcus, Staphylococcus*, and *Enterococcus*). The Gram-negative bacteria may include, but is not limited to, Gram negative rods (e.g., Bacteroidaceae, Enterobacteriaceae, Vibrionaceae, Pasteurellae and Pseudomonadaceae).

In another exemplary embodiment, the biomolecule is a surface molecule or surface antigen on the surface of a pathogen (e.g., a bacterial cell), or the biomolecule is a toxin or other byproduct of a pathogen (e.g., a toxin produced by a bacterial cell). Other examples of biomolecules are viral projections such as Hemagglutinin and Neuraminidase.

Use of the phrase "peptides", "polypeptide", or "protein" is intended to encompass a protein, a glycoprotein, a polypeptide, a peptide, fragments thereof and the like, whether isolated from nature, of viral, bacterial, plant, or animal (e.g., mammalian, such as human) origin, or synthetic, and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

Use of the phrase "polynucleotide" is intended to encompass DNA and RNA, whether isolated from nature, of viral, bacterial, plant or animal (e.g., mammalian, such as human) origin, or synthetic; whether single-stranded or double-stranded; or whether including naturally or non-naturally occurring nucleotides, or chemically modified. As used herein, "polynucleotides" include single or multiple stranded configurations, where one or more of the strands may or may not be completely aligned with another. The terms "polynucleotide" and "oligonucleotide" shall be generic to polydeoxynucleotides (containing 2-deoxy-D-ribose), to polyribonucleotides (containing D-ribose), to any other type of polynucleotide which is an N-glycoside of a purine or pyrimidine base, and to other polymers in which the conventional backbone has been replaced with a non-naturally occurring or synthetic backbone or in which one or more of the conventional bases has been replaced with a non-naturally occurring or synthetic base. An "oligonucleotide" generally refers to a nucleotide multimer of about 2 to 100 nucleotides in length, while a "polynucleotide" includes a nucleotide multimer having any number of nucleotides greater than 1, although they are often used interchangeably.

Use of the term "affinity" can include biological interactions and/or chemical interactions. The biological interactions can include, but are not limited to, bonding or hybridization among one or more biological functional groups located on the first biomolecule and the second biomolecule. In this regard, the first (or second) biomolecule can include one or more biological functional groups that selectively interact with one or more biological functional groups of the second (or first) biomolecule. The chemical interaction can include, but is not limited to, bonding among one or more functional groups (e.g., organic and/or inorganic functional groups) located on the biomolecules.

As used herein, the terms "antibody" and "antibodies" can include, but are not limited to, monoclonal antibodies, multispecific antibodies, human antibodies, humanized antibodies, camelised antibodies, chimeric antibodies, single-chain Fvs (scFv), single chain antibodies, Fab fragments, F(ab') fragments, disulfide-linked Fvs (sdFv), and anti-idiotypic (anti-Id) antibodies (e.g., anti-Id antibodies to antibodies of the disclosure), and epitope-binding fragments of any of the above. In particular, antibodies include immunoglobulin molecules and immunologically active fragments of immunoglobulin molecules (i.e., molecules that contain an antigen binding site). Immunoglobulin molecules can be of any type (e.g., IgG, IgE, IgM, IgD, IgA and IgY), class (e.g., IgG1, IgG2, IgG3, IgG4, IgA1 and IgA2) or subclass. The antibodies may be from any animal origin including birds and mammals (e.g., human, murine, donkey, sheep, rabbit, goat, guinea pig, camel, horse, or chicken). The antibodies may be monospecific, bispecific, trispecific, or of greater multispecificity.

Discussion:

In accordance with the purpose(s) of the present disclosure, as embodied and broadly described herein, embodiments of the present disclosure, in one aspect, relate to surface-enhanced Raman spectroscopic (SERS) systems and methods of using the SERS systems to detect an analyte. The present disclosure provides, in general, methods and systems for the detection, analysis, and/or quantification of a biomolecule. One aspect, among others, provides methods and systems for the detection of a biomolecule using SERS systems including a SERS substrate including an array of nanostructures.

In particular, the SERS system of the present disclosure can be used to determine the presence, qualitatively and/or quantitatively, of one or more types of biomolecules, cells, toxins, drugs, viruses (e.g., different types, different strands of the same type, differences within strands of the same type, and the like), bacteria, explosives, nuclear wastes, contaminants, biohazards, and other chemical and biological compounds of interest. For clarity, this disclosure describes the use of the SERS system with biomolecules, but one skilled in the art would understand that the SERS system can be used to determine the presence, qualitatively and/or quantitatively, of other targets of interest such as those described above, to which a complimentary binding agent exists or can be designed. Embodiments of the present disclosure also relate to methods of using the SERS system to detect biomolecules in a sample. The SERS system can enhance the detection molecules (e.g., biomolecules) by a number of orders of magnitude (e.g., 5-12 orders of magnitude) in a reproducible manner.

In an embodiment, methods of the present disclosure provide for determining the presence, qualitatively and/or quantitatively, and distinguishing (e.g., a difference in the SERS spectra can be ascertained using methods such as, but not limited to, cluster analysis) between different types of viruses. In another embodiment, the methods of the present disclosure provide for determining the presence, qualitatively and/or quantitatively, and distinguishing between different strands of the same virus. In another embodiment, the methods of the present disclosure provide for determining the presence, qualitatively and/or quantitatively, and distinguishing between the same strands of the same virus, where one or both strands include a mutation. In another embodiment, the methods of the present disclosure provide for determining the presence, qualitatively and/or quantitatively, and distinguishing between different portions of the same strands of the same virus (e.g., differences in a conserved gene region). A cluster analysis can be used to distinguish between various virus spectra in each of the embodiments described above and in the Examples.

In an embodiment, methods of the present disclosure provide for determining the presence, qualitatively and/or quantitatively, and distinguishing (e.g., a difference in the SERS spectra can be ascertained using methods such as, but not limited to, cluster analysis) between different types of bacteria. For example, embodiments of the present disclosure are able to distinguish among bacterium (e.g., between $E.\ Coli$ and $S.\ Aureus$) based on at least the following: the ratio of the Adenine and Guanine band intensities.

In general, the SERS system includes an array of nanostructures on a substrate. In preferred embodiments, the nanostructure is a nanorod. In an exemplary embodiment, the nanostructure is functionalized with one or more binding agent(s) capable of binding (e.g., ionically covalently, hydrogen binding, and the like) or otherwise associating (e.g., chemically, biologically, etc.) with one or more analytes (e.g., biomolecule(s)) of interest.

The nanostructures can include, but are not limited to, nanorods, nanowires, nanotubes, nanospirals, combinations thereof, and the like, and uniform arrays of each. The nanostructures (e.g., nanorods) can be fabricated of one or more materials such as, but not limited to, a metal, a metal oxide, a metal nitride, a metal oxynitride, a metal carbide, a doped material, a polymer, a multicomponent compound, a compound (e.g., a compound or precursor compound (organic or inorganic compound) including a metal, a metal oxide, a metal nitride, a metal oxynitride, a metal carbide, a doped material), and combinations thereof. The metals can include, but are not limited to, silver, nickel, aluminum, silicon, gold, platinum, palladium, titanium, copper, cobalt, zinc, other transition metals, composites thereof, oxides thereof, nitrides thereof, silicides thereof, phosphides ($P^{3-}$) thereof, oxynitrides thereof, carbides thereof, and combinations thereof. In particular the materials can include one or more of the following: silver, gold, nickel, silicon, germanium, silicon oxide, and titanium oxide. The composition of the nanorods is the same as that of the materials described herein or a combination of the materials described herein, or alternative layers of each.

In an embodiment of the SERS substrate of the present disclosure, the nanostructure is a nanorod. In particular embodiments, the nanorod is formed in a uniform and aligned array on the substrate. The nanorod can have the dimensions and characteristics as described below. In particular, the nanorods (e.g., silver, nickel, silicon, and titanium oxide) are disposed on a planar substrate, such a glass or silicon slide or disk, or a non-planar substrate, such as an optical fiber, or other cylindrically symmetric substrates.

A method of making a SERS substrate of the present disclosure includes providing a substrate and depositing the nanorods on the substrate by a modified oblique angle deposition (OAD) technique/system or glancing angle deposition (GLAD). In an embodiment of a modified OAD technique, the OAD system can include a two-axis substrate motion apparatus in a physical vapor deposition (PVD) system (e.g., thermal evaporation, e-beam evaporation, sputtering growth, pulsed laser deposition, and the like) that operates at temperatures lower than the melting point of the material used to form the nanostructures. In an embodiment, the substrate motion system provides two rotation movements: one is the polar rotation, which changes angle between the substrate surface normal and the vapor source direction, and one is the azimuthal rotation, where the sample rotates about its center axis of rotation (e.g., normal principle axis). In some embodiments, the nanorods are disposed on a thin film (e.g., silver, nickel, silicon, and titanium oxide) or a multilayer thin film (e.g., layers of silver, nickel, silicon, and titanium oxide, composites thereof, and nitrides thereof) that is deposited onto those substrate prior to nanorod deposition.

At least one advantage of using the OAD system is that the nanostructures (e.g., nanorods) can be formed at temperatures compatible with substrates such as, but not limited to, optical fibers, waveguides, and the like. This is in contrast to other techniques that operate under conditions (e.g., high temperatures) that are not compatible with many substrates of interest. Another advantage of using the OAD system is that catalysts are not needed to form the nanostructures, in contrast to currently used technologies. Since a vacuum system is used, the purity of the nanorods is very high, and the vacuum system is compatible with conventional microfabrication processes.

In some embodiments the substrate is a planar (or flat) substrate, such as a silicon, quartz, or glass substrate. Planar substrates may also be made of materials including, but not limited to, semiconductors (e.g., Si, GaAs, GaAsP, and Ge), oxides (e.g., $SiO_2$, $Al_2O_3$), and polymers (e.g., polystyrene, polyacetylene, polyethylene, etc.). In other embodiments the substrate is a non-planar substrate such as a cylindrical or conical substrate (e.g., an optical fiber or pipette tip). The substrates can also be microfabricated or nanofabricated substrates, such as substrates with a regular array of micropatterns, such as a dot array, line array, or well array, or similar nanopatterns.

FIG. 1 illustrates an embodiment of an OAD system for a planar substrate 30 (FIG. 1B) and an embodiment of an OAD system for a non-planar substrate 10 (FIG. 1A). The OAD systems 10 and 30 include, but are not limited to, an evaporation source 12, a substrate 14 or 34, and a substrate manipulation mechanism (e.g., one or more motors) to move (e.g., rotate) the substrate relative to the evaporation source 12. A motor of the OAD system 10 can move the non-planar substrate 14 in a polar rotation 18, which changes the incident angle ($\theta$) between the substrate rotating axis (e.g., center axis of rotation) and the vapor source direction (e.g., vapor arrival line 22). The OAD system 30 for the planar substrate 34 also includes a motor for moving the planar substrate 34 in a polar rotation 38, which changes the incident angle ($\phi$) between the surface normal axis of the substrate (e.g., axis 40) and the vapor source direction (e.g., vapor arrival line 32).

Another motor of the OAD system 10 can move the substrate in an azimuthal rotation 16, where the sample rotates about its center axis of rotation (normal principle axis) to allow deposition of nanorods around entire surface of the non-planar substrate 14. In the case of a planar substrate 34, while azimuthal rotation of the substrate is not required for deposition of the nanorods, the OAD system 30 may optionally include a second motor for rotating the planar substrate in an azimuthal rotation 36, which allows additional control over the shape of the nanorods. For both planar and non-planar substrates, varying the incident angles $\theta$ and $\phi$ and the rate and pattern of azimuthal rotation can result in various shapes, sizes, and/or distribution of nanorods on the substrate surface. The OAD systems 10 and 30 can also include appropriate vacuum pumps and electronic control equipment as are known in the art. Additional details regarding the OAD systems are described in the Examples below.

Embodiments of the OAD systems 10 and 30 can include a physical vapor deposition (PVD) system, such as thermal evaporation, e-beam evaporation, molecular beam epitaxy (MBE), sputtering growth, pulsed laser deposition, combinations thereof, and the like. In this embodiment, the PVD is a thermal evaporation source 12, where a material can be heated to an appropriate temperature to evaporate the material. The heating temperature depends primarily on the properties of the material to be deposited, but may also depend, at least in part, on the substrate 14 or 34, and other conditions in the OAD system. Typically, the temperature is less than the melting point (e.g., less than one-third of the melting point) of the material being evaporated.

In an alternative embodiment, the system can be adapted to include a Chemical Vapor Deposition (CVD) or a Plasma-Enhanced Chemical Vapor Deposition (PECVD) system. In such systems an appropriate molecular precursor is evaporated at the source and undergoes decomposition at the surface of the substrate 14 or 34. The decomposition leads to the deposition of a material of interest onto the substrate 14 or 34 with concomitant elimination of molecular fragments, which can be easily purged from the system. CVD and PECVD allow for the single-step deposition of unitary- (e.g., metals), binary- (e.g., alloys, oxides, carbides), ternary- (e.g., (Si,Ge)$O_4$), and higher other compounds.

Modification of the system for use in conjunction with CVD and PECVD deposition techniques can be inferred from standard CVD and PECVD systems described in the art (e.g., D. M. Dobkin, M. K. Zuraw, *Principles of Chemical Vapor Deposition*, (2003) Springer, NY.; Srinivasan Sivaram, *Chemical Vapor Deposition: Thermal and plasma deposition of electronic materials (Electrical Engineering)*, (1995), Springer NY).

The OAD systems can operate at a substrate temperature less than the melting point of the material being evaporated. In particular, the substrates of the OAD systems can operate at or near room temperature, be cooled to liquid nitrogen temperature, or be heated to a temperature of about ⅓ of the melting temperature of the material being evaporated. Thus, substrates having a relatively low melting point (e.g., plastics such as those used in fiber optics) can be used, unlike other high temperature techniques. The OAD systems can operate at a pressure where the mean free path of the gas in the chamber during deposition is comparable or larger than the source-substrate distance.

The substrate 14 and/or 34 can be mounted or otherwise attached to an arm or other component in communication with the motors that move the substrate. In one embodiment, to deposit nanostructures (e.g., nanorods) onto a non-planar substrate 14, the substrate 14 is slightly rotated polarly in order to make an angle $\theta$ less than about 15° (e.g., $\theta$ less than about 12°, $\theta$ less than about 10°, $\theta$ less than about 8°, and $\theta$ less than about 5°; and where $\theta$ is from about $\theta$, about 0 to 12°, about 0 to 10°, about 0 to 8°, and about 0 to 5°), with respect to the incoming vapor direction. Then, the source material is evaporated at a constant rate (e.g., the rate is about 0.1 nm/sec to 0.3 nm/sec, about 0.1 nm/sec to 0.6 nm/sec, about 0.1 nm/sec to 1 nm/sec, about 0.1 nm/sec to 1.5 nm/sec, and about 0.1 nm/sec to 2 nm/sec), or substantially constant rate, in the evaporation source 12, while the substrate 14 is rotated with a constant speed azimuthally (e.g., the speed is about 0.01 rev/sec to 0.05 rev/sec, about 0.01 rev/sec to 0.1 rev/sec, about 0.01 rev/sec to 0.2 rev/sec, and about 0.01 rev/sec to 0.4 rev/sec). The nanostructures of the evaporated material are thereby deposited (e.g., uniformly deposited) onto the sidewall (e.g., the inner and/or outer sidewall or selected portions thereof) of the substrate.

Such non-planar substrates are symmetrical about one center axis of rotation. The non-planar surface can be an inside surface and/or an outside surface of the substrate. The non-planar surface can include, but is not limited to, a cylindrical surface, a tapered surface, a conical surface, a tapered cylindrical surface, a cylindrical ringed substrate, and the like. The length of the substrate can be from about 1 mm to about 75 mm. The diameter of the substrate can be about 1 mm to about 75 mm. Exemplary substrates include, but are not limited to, optical fibers, waveguides, glass tubes, capillary tubes, metallic rods/tubes, and the like. Methods of forming nanostructure arrays on non-planar surfaces is described in greater detail in U.S. patent application Ser. No. 11/256,395, which is incorporated by reference herein.

In another embodiment, to deposit nanostructures (e.g., nanorods) onto a planar substrate 34 (e.g., a glass microscope slide), the substrate is mounted to the OAD device 30, as shown in FIG. 1B. Depending on the size of the OAD system, the size of the substrate may vary from about 1×1 $mm^2$ to about 30×30 $cm^2$. In some embodiments, it is preferable to deposit one or more thin film base layers of material (such as the materials described above for forming the nanostructures) on the substrate. This can be accomplished by first positioning the substrate at a normal incidence (e.g., $\phi=0°$) to the evaporation source (e.g., where the substrate is face down to the evaporation source). A thin film base layer, or multilayer thin film base layer, may also be deposited on non-planar substrates by first positioning the substrate with the central axis of rotation perpendicular to the vapor line of arrival 22 from the evaporation source 12 (e.g., $\theta=90°$), while continually rotating the substrate azimuthally at a constant rate of rotation. Additional details of the thin film are described below. In some embodiments the thickness of the film is from about 10 nm to about 1000 nm; in a particular embodiment it is between about 50 nm and about 500 nm. To deposit the nanorods on the planar substrate 34, the substrate is then rotated polarly in order to make an incident angle $\phi$ less than about 89° (e.g., where $\phi$ is from about 75° to 89°, about 80° to 86°, and about 86°), of the surface normal of the substrate with respect to the incoming vapor direction.

The nanorods are then deposited on the planar substrate by oblique angle vapor deposition. The source material is evaporated at a constant rate (e.g., the rate is about 0.1 nm/sec to 0.3 nm/sec, about 0.1 nm/sec to 0.6 nm/sec, about 0.1 nm/sec to 1 nm/sec, about 0.1 nm/sec to 1.5 nm/sec, and about 0.1 nm/sec to 2 nm/sec), or substantially constant rate, in the evaporation source 12, while the substrate 34 is optionally rotated azimuthally. The speed can be constant, or can vary, depending on the shape of the nanostructures desired (e.g., the speed is about 0.01 rev/sec to 0.05 rev/sec, about 0.01 rev/sec to 0.1 rev/sec, about 0.01 rev/sec to 0.2 rev/sec, and about 0.01 rev/sec to 0.4 rev/sec). The nanostructures of the evaporated material are thereby deposited (e.g., uniformly deposited) onto the surface of the substrate.

The temperature, the pressure, the deposition rate, the angle of vapor incidence, the evaporating material, and the speed and direction of the azimuthal rotation can be adjusted to control the properties of the nanostructures (e.g., the length, diameter, density, composition, and the like). Additional details regarding the process are described in the following Examples.

In some embodiments of methods of making the SERS substrates of the present disclosure, the nanorods are deposited in steps including exposing a first portion of a substrate to a metal vapor (e.g., via chemical metal vaporization) by opening a shutter 42 to a first setting. The first setting exposes a predetermined portion of the substrate. A first nanorod at a first position on the substrate is formed. The first nanorod grows to a first height (e.g., about 200 nanometers). Subsequently, the shutter is opened to a second setting, thereby exposing the first portion and a second portion to the metal vapor. A second nanorod is formed at a second position on the substrate. The second nanorod grows to the first height (e.g., about 200 nanometers). In this step the first nanorod grows to a second height (e.g., 400 nanometers), where the second height is about twice as high as the first height. This process can be repeated to expose a plurality of portions on the substrate to create a plurality of nanorods of various lengths on the substrate. For example, nanorods of the following lengths can be prepared: about 200 nanometers, about 400 nanometers, about 600 nanometers, about 800 nanometers, and about 1000 nanometers.

The length is the largest dimension of the nanostructure and is the dimension extending from the substrate (FIGS. 2A-E). The length/height of the nanorod can be from a few hundred nanometers or less to over a few thousand nanometers. In embodiments, the nanostructure can have a length of about 10 nm to 10000, about 10 nm to 5000 nm, about 10 nm to 4000 nm, about 10 nm to 3000 nm, about 10 nm to 2000 nm, about 10 nm to 1000 nm, about 10 nm to 500 nm, about 10 nm to 250 nm, about 10 nm to 100 nm, and about 10 nm to 50 nm. In particular, the nanostructures can have a length of about 100 nm to about 1500 nm. The length depends, at least in part, upon the deposition time, deposition rate, and the total amount of evaporating materials. The substrate can have nanorods of the same height or of varying heights on one or more portions of the substrate.

The diameter is the dimension perpendicular to the length. The diameter of the nanostructure is about 10 to 30 nm, about 10 to 60 nm, about 10 to 100 nm, about 10 to 150 nm. In particular, the nanorods can have a diameter of about 50 to 120 nm. One or more of the dimensions of the nanostructure could be controlled by the deposition conditions and the materials.

The substrate can have from tens to tens of thousands or more nanorods formed on the substrate. The array of nanostructures can be defined as having a distance of about 10 to 30 nm, about 10 to 60 nm, about 10 to 100 nm, about 10 to 150 nm, and about 10 to 200 nm, between each of the nanostructures. Alternatively, the array of nanostructures can be defined as having an average density of about 11 to 2500 $\mu m^2$. The number of nanorods, height and diameter of the nanorods, and the material that the nanorods of fabricated of will depend upon the specific application of the SERS system.

In embodiments of the SERS substrates of the present disclosure, as illustrated in FIG. 2A, the nanorods also have a tilt angle, β, formed between the nanostructure 102 and the substrate 106. The angle β is less than 90°, particularly from about 0° to about 50°, and in preferred embodiments can be from about 5° to about 20°, from about 15° to about 30°, and from about 25° to about 40°. The conditions and the materials used to prepare the nanostructure 102 can be used to determine/select the tilt angle. The tilt angle is important in creating SERS enhancement factors with sufficient sensitivity to detect binding of an analyte of interest to the SERS sensors of the present disclosure.

It should also be noted that the nanostructure could have multiple layers of different materials or alternating materials. FIGS. 2A and 2B illustrate nanostructures (e.g., nanorods) fabricated from two and three materials, respectively. In particular, FIG. 2A illustrates a nanostructure 102 disposed on a substrate 100 having a surface 106. The nanostructure 102 includes two layers of different materials 104a and 104b. The materials can be any combination of the materials described herein. The dimensions of the nanostructure 102 can include those described herein. In another embodiment, additional layers of materials can be formed on the nanostructure 102, as shown in FIG. 2B. For example, a repeating pattern of layers 104a and 104b can be created, or three layers 114a, 114b, and 114c of a nanostructure 112 can be created (FIG. 2B).

FIG. 2C illustrates a nanostructure 122 disposed on a substrate 120 having a surface 126. The nanostructure 122 includes three layers of one or more materials 124a, 124b, and 124c, in a zig-zag pattern. The dimensions of the nanostructure 122 can include those described herein. The zig-zag nanostructure can be created by changing the angle periodically from $\phi_1$ to $\phi_2$ (or from $\theta_1$ to $\theta_2$, in the case of non-planar substrates) during vapor deposition to change the tilt angle β of the nanostructure being formed. The material for layers 124a, 124b, and 124c can be the same material, or can be two or more different materials.

Figure 2D:
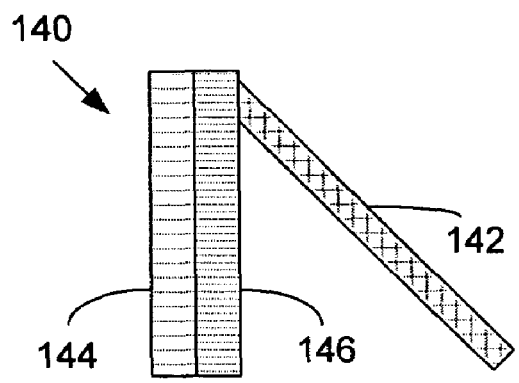

FIG. 2D illustrates a nanostructure 142 disposed on a layer 146 disposed on a substrate 140 having a surface 144. The layer 146 can be made of a materials such as those described herein for forming the nanostructures, such as, but not limited to, a metal, a metal oxide, a metal nitride, a metal oxynitride, a doped material, a polymer, a multicomponent compound, and combinations thereof. The layer 146 can have a thickness of about 10 to 50 nm, about 10 to 100 nm, about 10 to 200 nm, about 10 to 500 nm, about 10 to 800 nm, about 10 to 1000 nm, and about 10 to 2000 nm. The dimensions of the nanostructure 142 can include those described herein. The layer 146 can be made by changing the incident angle φ first to 0° (in the case of non-planar substrates, θ to 90°), depositing a uniform first layer 146 by continuous azimuthal rotation. Then, angle φ is changed to a larger angle (or angle θ is changed to a smaller angle) to deposit nanostructure 142 on top of the film 146.

Figure 2E:
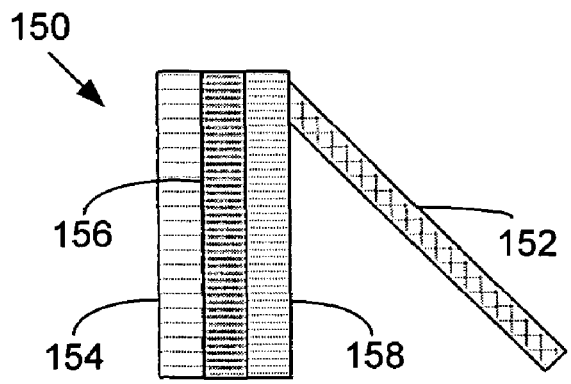

FIG. 2E illustrates a nanostructure 152 disposed on a second layer 158 disposed on a first layer 156 that is disposed on a substrate 150 having a cylindrical surface 154. The first and second layers 156 and 158 can each be made of a material, such as, but not limited to, a metal, a metal oxide, a metal nitride, a metal oxynitride, a doped material, a polymer, a multicomponent compound, and combinations thereof. The first and second layers 156 and 158 can each have a thickness of about 10 to 50 nm, about 10 to 100 nm, about 10 to 200 nm, about 10 to 500 nm, about 10 to 800 nm, about 10 to 1000 nm, and about 10 to 2000 nm. The dimensions of the nanostructure 152 can include those described herein. The first and second layers 156 and 158 can be made by changing the incident angle φ first to 0° (in the case of non-planar substrates, θ to 90°), depositing a uniform first layer 156 by continuous azimuthal rotation, and subsequently depositing a uniform second layer 158 by continuous azimuthal rotation.

Then, angle φ is changed to a larger angle (or angle θ is changed to a smaller angle) to deposit nanostructure 152 on top of the second layer 158.

Additional combinations of uniform layer(s), nanorods with layers of multiple materials, and shaped nanorods are described in U.S. patent application Ser. No. 11/256,395, which is incorporated by reference herein. The nanostructures can also be formed in various shapes by varying the incident angle φ or θ and/or varying the speed, direction, and/or pattern of azimuthal rotation as described in Y. P. Zhao, D. X. Ye, Pei I. Wang, G. C. Wang, and T. M. Lu, "*Fabrication Si nano-columns and square springs on self-assembly colloid substrates*," International Journal of Nanoscience 1, 87 (2002); and Y.-P. Zhao, D.-X. Ye, G.-C. Wang, and T.-M. Lu, "*Designing nanostructures by glancing angle deposition*," SPIE Proceedings Vol. 5219, 59 (2003), which are hereby incorporated by reference herein in their entirety.

Figure 3A:
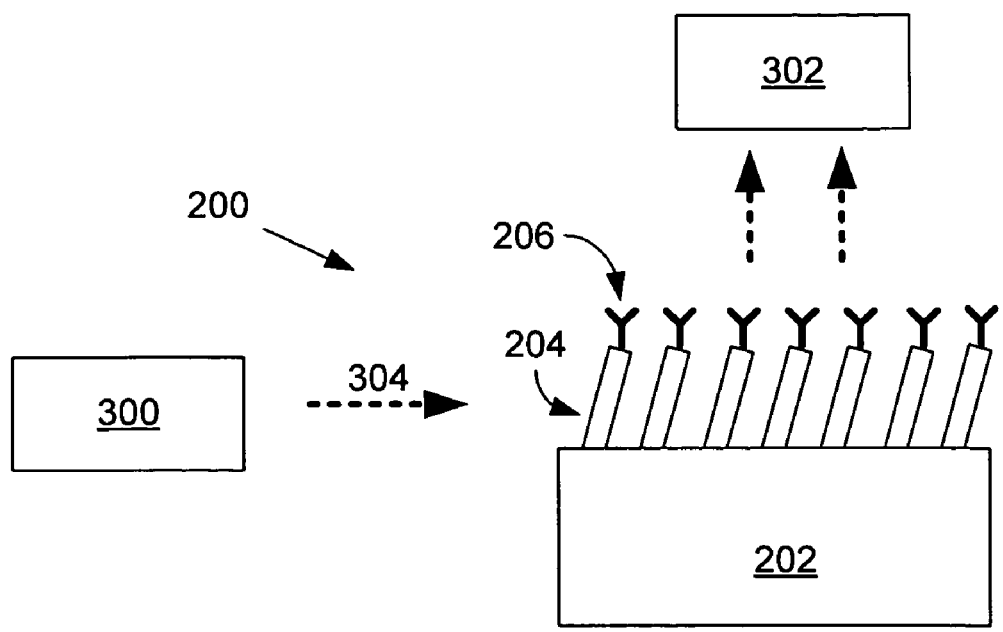
FIGS. 3A through 3B illustrate exemplary schematics of a SERS system according to the present disclosure having nanostructures deposited on the surface or portions of the surface of a substrate and a binding agent attached to the surface of the nanostructures (FIG. 3A), which is capable of binding a target analyte (FIG. 3B).

As illustrated in the SERS system 200 of FIG. 3A, once the nanorods 204 are formed on the substrate 202, a binding agent 206, such as a biomolecule, is disposed on one or more of the nanorods 204. The binding agent 206 is generally a biomolecule (as defined above), such as, a polynucleotide, polypeptide, carbohydrate, lipid, or the like. Exemplary polypeptide binding agents include, but are not limited to, antibodies or fragments thereof. The binding agent 206 can be attached/coupled to a surface of the nanostructure 204 using conventional linking chemistry (e.g., biologically (e.g., hybridization) and/or chemically (e.g., ionically or covalently)). For instance, the nanorods 204 can be functionalized by immobilizing the binding agent 206 (e.g., an antibody) on the nanorod surface by annealing to the metal (e.g., Ag or Au) surface of the nanorod via a linking agent (e.g., DSP (dithiobis(succinimidyl propionate)) or SAM (self-assembly monolayer)). Additional details regarding the disposition of the binding agent on the nanostructures are provided in the examples below.

A single type (e.g, the same polymer sequence) of binding agent 206 can be disposed or otherwise attached to the nanorods 204 on the substrate 202 (e.g., on the nanorods) or a plurality of types (e.g., two or more different polymer sequences) of binding agent can be disposed on the one or positions of the substrate.

Figure 3B:
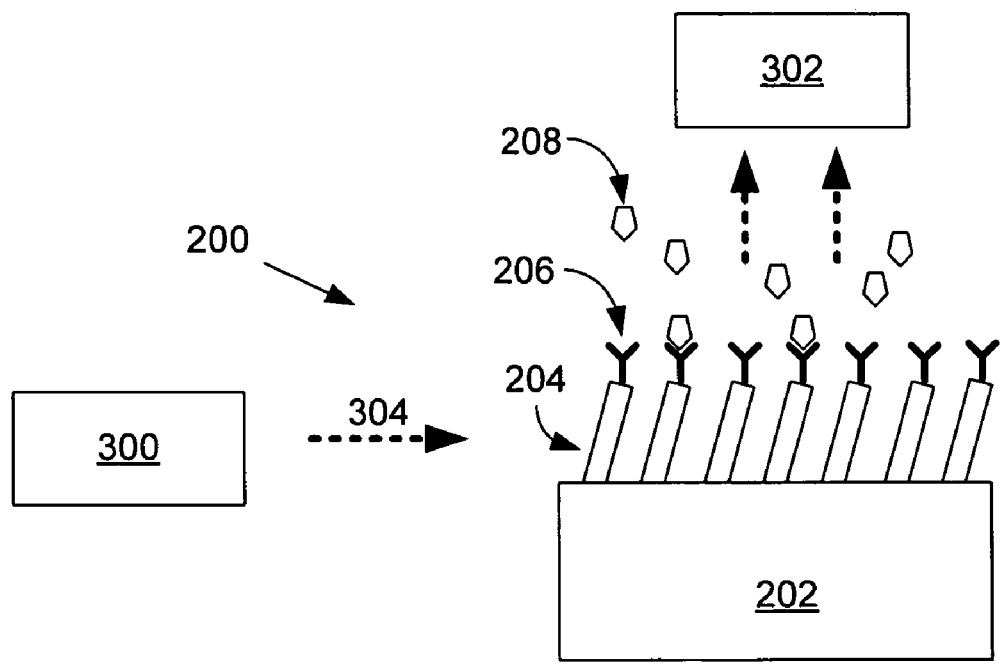

Typically, the binding agent 206, or first biomolecule, is disposed in an area of the substrate 202 having a plurality of nanorods 204. The array of nanorods 204 in combination with the first biomolecule 206 has a first measurable surface-enhanced Raman spectroscopic signature. Then, as illustrated in FIG. 3B, when an analyte of interest 208, such as a biomolecule (e.g., a second biomolecule), is introduced to the SERS system 200, the biomolecule 208 binds or otherwise interacts with the binding agent 206 bound to the nanostructure 204. Generally, the biomolecule 208 can be present or believed to be present in a sample, such as a gasseolus, tissue or fluid sample. Exemplary samples include buccal cells, buffered solutions, saliva, sweat, tear, phlegm, urine, blood, plasma, cerebrospinal fluid, or combinations thereof.

The binding agent/first biomolecule 206 has an affinity for a second biomolecule 208. If the second biomolecule 208 bonds or otherwise attaches to the first biomolecule 206, the array of nanorods 204 in combination with the first biomolecule 206 and the second biomolecule 208 has a second measurable surface-enhanced Raman spectroscopic signature that is different (e.g., a statically significant difference, in that it is unlikely to have occurred randomly or by chance) than first measurable surface-enhanced Raman spectroscopic signature. Therefore, the interaction of the first biomolecule 206 and the second biomolecule 208 can be measured using the SERS system 200. Additional details regarding the detection of a second biomolecule binding event by measuring the surface-enhanced Raman spectroscopic signatures are provided in the Examples below.

Figure 3C:
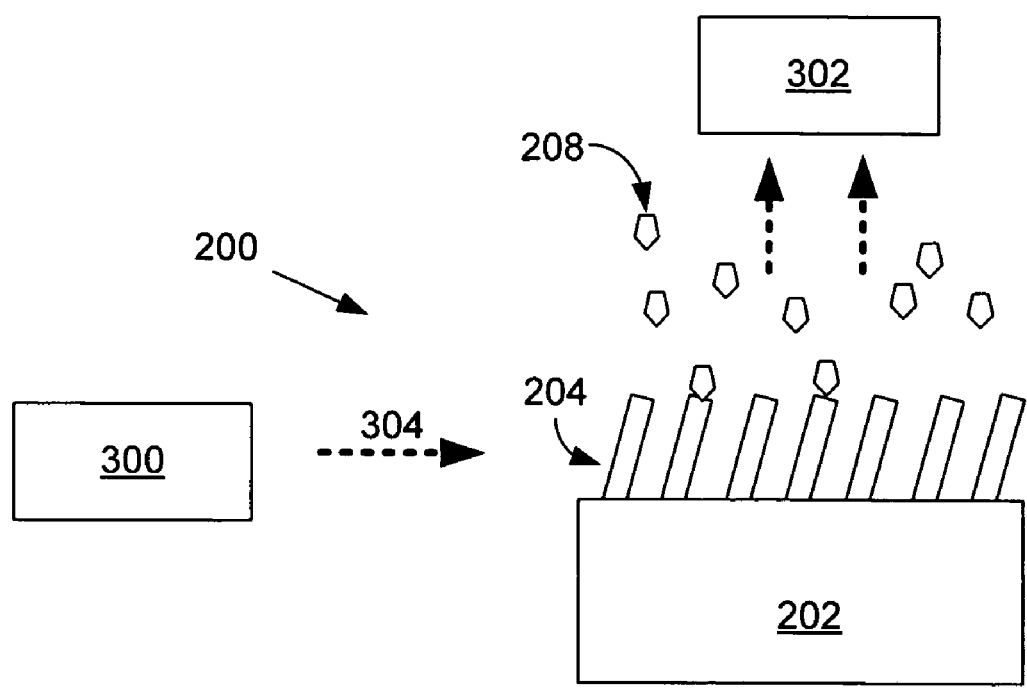
FIG. 3C is an exemplary schematic illustration of an embodiment of a SERS system according to the present disclosure having nanostructures deposited on the surface or portions of the surface of a substrate, which are capable of binding and detecting a target analyte directly, without a binding agent.
Figure 13:
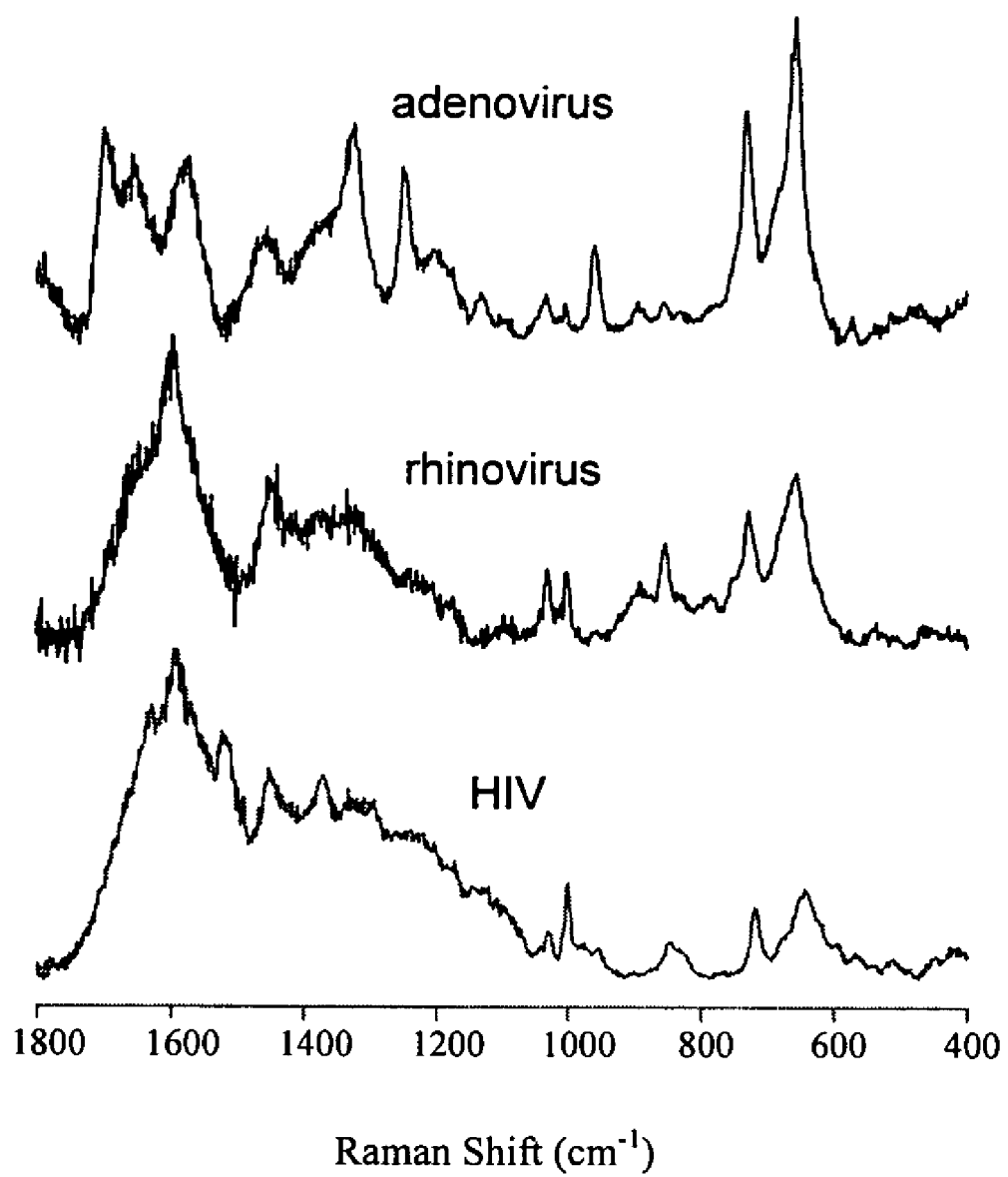
FIG. 13 illustrates a SERS spectra of adenovirus (top), rhonovirus (middle), and HIV (bottom) on an Ag nanorod array substrate, without a binding agent.

In other embodiments of the SERS system 200, as illustrated in FIG. 3C, the analyte of interest 208 (e.g., a biomolecule including, but not limited to, a virus, bacterium, or other pathogen or fragment thereof) can be disposed directly on the nanorods 204. A particular biomolecule of interest can be detected because individual biomolecules of interest have a unique SERS spectra that is detectably different, and thus distinguishable, from the SERS spectra of other biomolecules, as demonstrated in Example 4 and FIGS. 13-16, below. For example, the SERS spectra of adenovirus is distinguishable from that of rhinovirus and HIV, as illustrated in FIG. 13. Individual strains of virus can even be distinguished in this way, as demonstrated with three strains of influenza in Example 5 and FIG. 16, below. Thus, individual biomolecules, such as viruses, have a unique SERS "fingerprint" that allow a particular biomolecule of interest to be distinguished from other biomolecules or background media.

Embodiments of the SERS system 200, also include an excitation source 300. The excitation source includes, but is not limited to, illumination sources such as a diode laser and an optical fiber laser, dye laser, solid state laser. In some embodiments, the excitation source 300 provides a stream of incident light 304 directed to the SERS substrate 202 to provide excitation for generating the Raman signal. In preferred embodiments the incident light 304 is perpendicular to the nanorods 204, as illustrated in FIG. 3B. The SERS system 200, also may include a data collection and analysis system, such as an optical data collection port 302 for collecting the Raman signal produced by the excitation of the SERS substrate and a system for producing the SERS spectra. Additional details regarding the excitation source and SERS data collection and analysis systems are provided in the examples below.

As mentioned above, embodiments of the present disclosure provide SERS systems and methods for determining the presence, qualitatively and/or quantitatively, and distinguishing between different types of viruses and virus strains. In general, the SERS systems and methods of use thereof can measure SERS spectra of different viruses (i.e. RNA or DNA viruses). The SERS system can measure detectably different (e.g., a difference in the SERS spectra can be ascertained using methods such as, but not limited to, cluster analysis) features between the viruses. In particular, each virus can have a measurable surface-enhanced Raman spectroscopic signature, where the signature of each virus are distinguishable and include detectably different features.

As mentioned above, embodiments of the present disclosure provide SERS systems and methods for determining the presence, qualitatively and/or quantitatively, for distinguishing between different nucleotide patterns and surface proteins between viruses and in virus strains. The SERS system can measure detectably different features between the different viruses based on a measurable surface-enhanced Raman spectroscopic signature, where the signature of each virus is distinguishable and include detectably different features.

As mentioned above, embodiments of the present disclosure provide SERS systems and methods for determining the presence, qualitatively and/or quantitatively, and distinguishing between the same strands of the same virus, where one or both strands include a mutation. In general, the SERS system and methods of use thereof can measure SERS spectra of two or more nucleic acid strands of the same virus, where one or both strands include a mutation. The SERS system can measure detectably different features between the different strands of the same virus. In particular, each strand of the virus can have a measurable surface-enhanced Raman spectroscopic signature, where the signature of each strand of the virus are distinguishable and include detectably different features.

As mentioned above, the methods of the present disclosure provide for determining the presence, qualitatively and/or quantitatively, and distinguishing between different portions of the same strands of the same virus (e.g., differences in a conserved gene region). In general, the SERS system and methods of use thereof can measure SERS spectra of two or more of the same nucleic acid strands of the same virus. The SERS system can measure detectably different features between the different strands of the same virus. In particular, each strand of the virus can have a measurable surface-enhanced Raman spectroscopic signature, where the signature of each strand of the virus are distinguishable and include detectably different features.

As mentioned above, embodiments of the present disclosure provide SERS systems and methods for determining the presence, qualitatively and/or quantitatively, and distinguishing between different types of bacterium. In general, the SERS systems and methods of use thereof can measure SERS spectra of different bacteria. The SERS system can measure detectably different (e.g., a difference in the SERS spectra can be ascertained using methods such as, but not limited to, cluster analysis) features between the bacteria. In particular, each bacterium can have a measurable surface-enhanced Raman spectroscopic signature, where the signature of each bacterium are distinguishable and include detectably different features.

It should be emphasized that the above-described embodiments of the present disclosure, particularly, any "preferred" embodiments, are merely possible examples of implementations, and are merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

EXAMPLES

Example 1

Sample Preparation

All of the samples were prepared using an electron beam/sputtering evaporation system (E-beam) that was custom built by Torr International. A schematic of the set-up is shown in FIG. 1A. A glass microscope slide with size 1×3" and 1 mm thick (Gold Seal®) was used as a substrate 34. A custom shutter 42 was built that could be controlled externally by a feed through, and the shutter was used to selectively reveal increasing portions of the substrate 34 during the deposition process. This method can produce one single sample with 6 different active areas. As an example, one particular sample had a 50 nm thin film deposited at normal incidence and then it was rotated to an incident angle 4 of 86°. Then nanorods were deposited in steps of 200 nm; i.e. the shutter 42 was opened partially and 200 nm was deposited, then the shutter was opened slightly more exposing more of the substrate and another 200 nm was deposited while keeping the previously exposed area still open making two sections one with 200 nm rods and one with 400 nm. This was repeated until a total of 1000 nm was reached for the first open area. The purpose of this particular setup is to achieve an environment in which all experimental conditions are the same for each different rod length. In a conventional setup (one rod length per sample, per run), the time needed to complete the experiments would be 5 days opposed to 1 day.

The background pressure was $4.5 \times 10^{-6}$ Torr for, and the base temperature was 48.5° C. The source to substrate distance was approximately 12". The deposition was divided into two sections: the first was depositing the 50 nm thin film at a rate of 0.4 Å/s, and the second was depositing the rods at a rate of 2.0 Å/s. The schematic of the resulting film and nanorod is shown in FIG. 2D.

Figure 4:
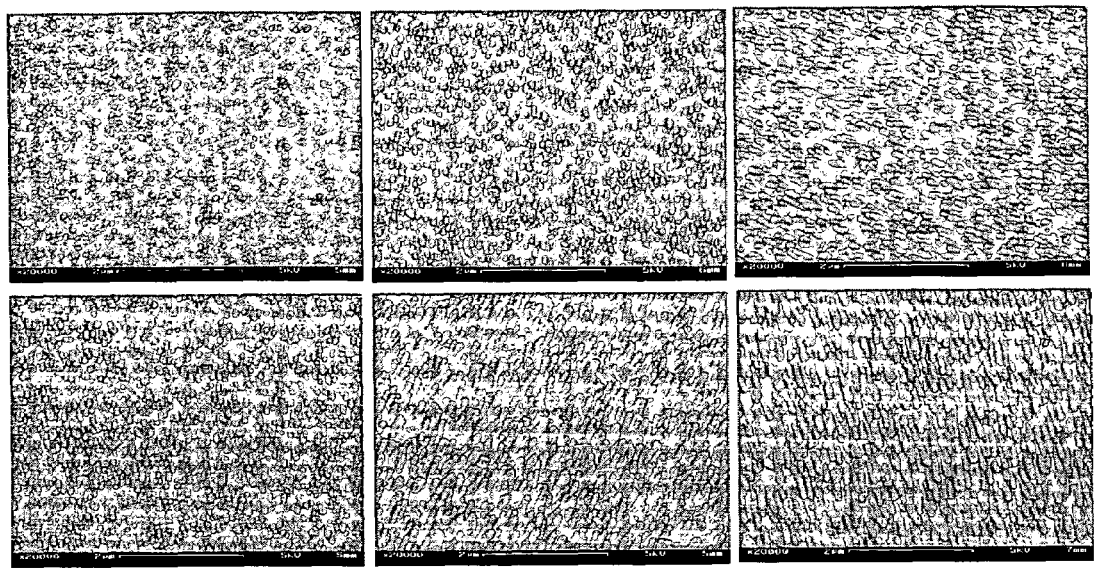
FIG. 4 illustrates SEM images of various length nanorods on a planar substrate.
Figure 5:
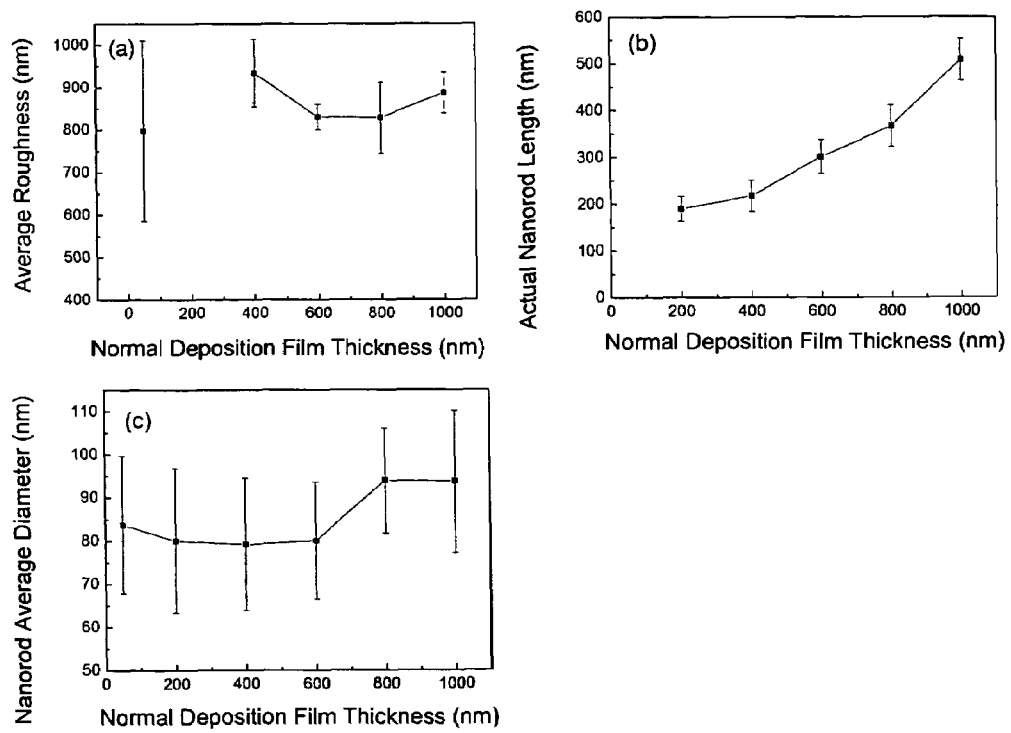
FIG. 5 illustrates various nanorod parameters (a) RMS roughness, (b) nanorod length, and (c) nanorod diameter as functions of normal deposition thickness.

The actual length and density of the rods were measured using Scanning Electron Microscopy (SEM), and the roughness of the surfaces was measured using Atomic Force Microscopy (AFM). FIG. 4 shows the SEM images of the nanorods at different section on the substrate. The average roughness, diameters, and actual lengths of each section of nanorods are displayed in the graphs illustrated in FIG. 5.

The actual rod length denotes the fact that when depositing at an angle of about 86°, the deposition rate displayed by the thickness monitor is not the same as the amount of material actually deposited onto the substrate due to a reduced flux. The diameter is representative of the average width of the tips of several hundreds of rods at a given length.

SERS Measurements:

Surface Enhanced Raman spectra were acquired using a Kaiser Optical Systems confocal Raman microscope (Kaiser Optical Systems Incorporated, Ann Arbor, Mich.) equipped with a liquid nitrogen cooled Charge Coupled Device (CCD) camera (Princeton, Instruments, Trenton, N.J.). The spectrograph used was a Holospec f/1.8-NIR spectrometer equipped with a HoloPlex grating that simultaneously measures the range of 100 to 3450 $cm^{-1}$ at an excitation wavelength of 785 nm illumination supplied by a Coherent Radiation 899 Ti:Sapphire Ring Laser (Coherent, Santa Clara, Calif.) pumped by a Coherent Radiation Innova 300 Series $Ar^+$ laser (Coherent, Santa Clara, Calif.). SERS spectra were collected with ~20 mW laser power at the sample under the microscope objective.

All spectra were collected using the Holograms 4.0 software supplied by the manufacturer. Post processing of the collected spectra was performed using GRAMS32/AI spectral software package (Galactic Industries, Nashua, N.H.). Center of Gravity calculations were made using a GRAMS32 based program written in our laboratory (R. A. Dluhy, unpublished). All spectra were baseline corrected for clarity.

Figure 6:
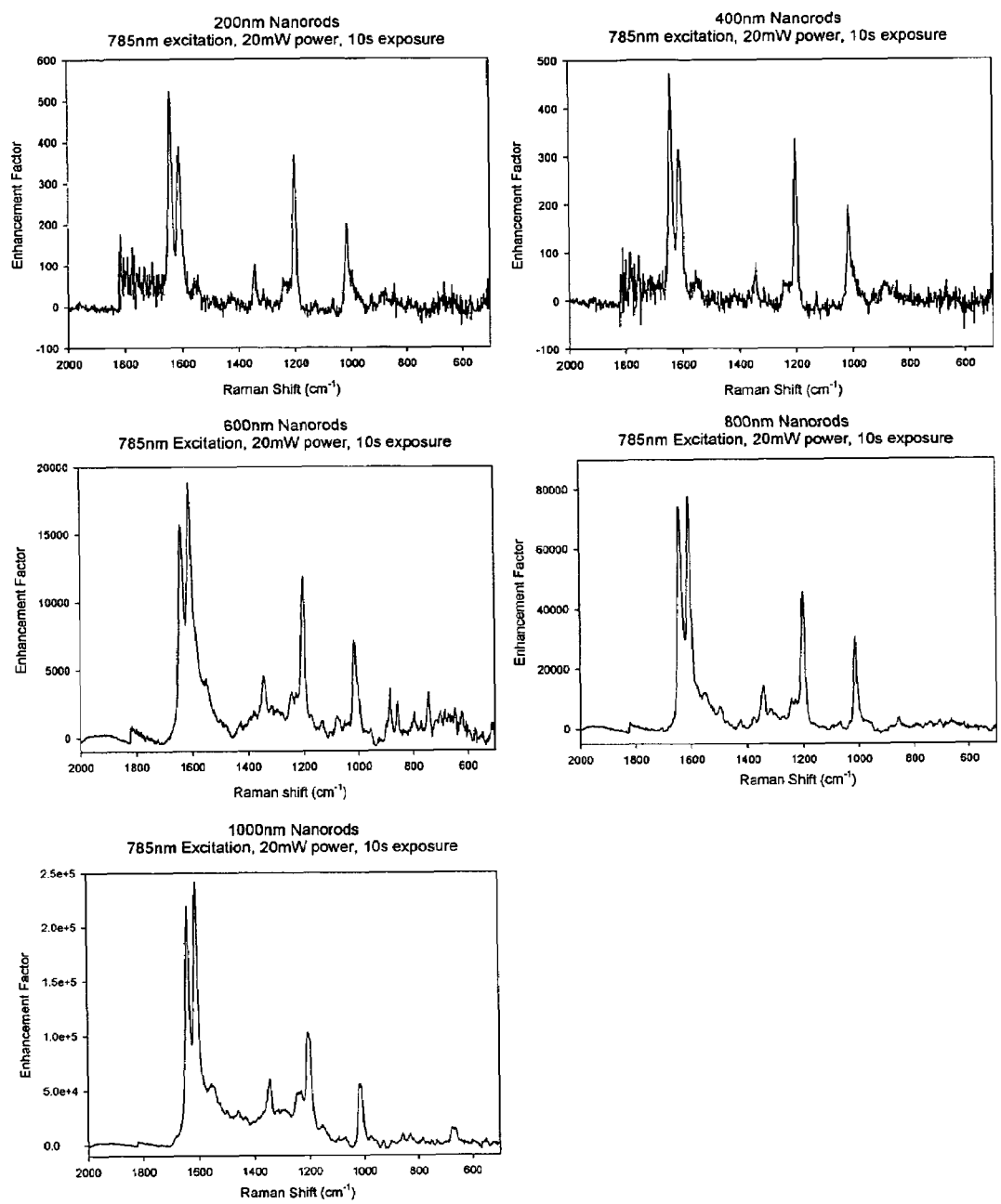
FIG. 6 illustrates SERS spectra for samples having various length nanorods.

The molecular probe used in this study was trans-1,2-bis (4-pyridyl)ethene (BPE, Aldrich, 99.9+%). BPE solutions were prepared by sequential dilution of HPLC grade methanol (Aldrich). BPE solution was applied to each of the SERS substrates and allowed to dry before the acquisition of spectra. The concentration of the BPE and the volume applied were calculated so as to produce a surface coverage of about 0.21 monolayers (assuming $7 \times 10^{64}$ BPE molecules per $cm^2$ in a monolayer). It has been observed that at greater monolayer coverage the SERS intensity drops off significantly. This drop-off has been attributed to inter-adsorbate interactions and coverage-dependent dielectric interactions. Spectra were acquired for about 10 s and obtained for multiple spots on each substrate. BPE was chosen as the probe to calculate enhancement factors because of its high Raman scattering cross-section and its ability to adsorb strongly and irreversibly to the Ag substrate. The 1200 $cm^{-1}$ peak of BPE was chosen for the quantification because of its relative insensitivity to molecular orientation on a Ag surface. FIG. 6 shows the SERS spectroscopy of different samples with different nanorod lengths.

Calculation of Surface Enhancement Factor

The Surface Enhancement Factor (SEF) is defined as the ratio of the integrated intensities contributed by the molecules on the surface and in the solution, respectively.

$$SEF = \frac{I_{surf}/N_{surf}}{I_{bulk}/N_{bulk}}$$

where $I_{surf}$ and $I_{bulk}$ denote the integrated intensities for the 1200 cm$^{-1}$ band of the BPE adsorbed on the Ag surface and BPE in solution respectively, whereas $N_{surf}$ and $N_{bulk}$ represent the corresponding number of BPE molecules excited by the laser beam. Thus from the surface Raman signal detected, the solution spectrum, and the solution concentration, the Surface Enhancement Factor was calculated for the different SERS substrates.

$N_{surf}$ was calculated using the following approximation:

$$N_{surf} = A_{substrate} \times 0.21 \times 7 \times 10^{14} \times \pi a^2$$

where $A_{substrate}$ is the geometric area of the SERS substrate (in cm$^2$); and a is the radius of the laser focal spot.

$N_{bulk}$ was calculated using the following approximation:

$$N_{bulk} = \pi a^2 h c N_A$$

where c is the concentration of the BPE solution in the cuvette; h (in μm) is the confocal depth; and $N_A$ is the Avogadro number.

$I_{surf}$ and $I_{bulk}$ were calculated from the integrated area under the 1200 cm$^{-1}$ band in the BPE spectrum using a Center of Gravity algorithm written by the present investigators in the GRAMS32 environment.

Figure 7:
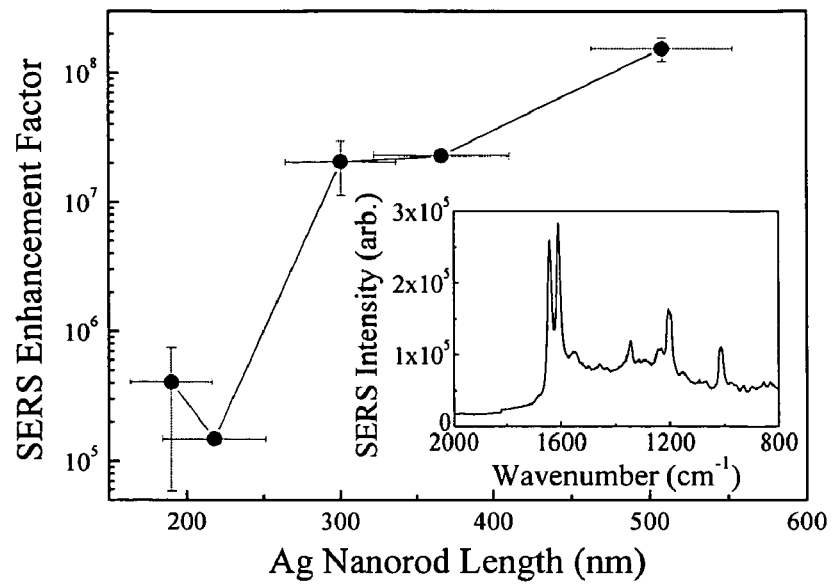
FIG. 7 illustrates a graph of the SERS enhancement factor relative to the length of the nanorods.

Surface Enhancement Factors (EF) were calculated for each of the spectra collected on all the SERS substrates and were plotted with error bars against the nanorod length. FIG. 7 shows the actual EF versus nanorod length.

Example 2

This example describes a method to prepare nanostructured SERS substrates that allow for rapid and sensitive detection of the molecular fingerprint of RNA and DNA viruses using Raman spectra, as well as providing structural and quantitative information about the viruses.

Development of diagnostic methods for rapid and sensitive identification of viruses is essential for defining the emergence of viral infection, determining the period that preventive measures should be applied, for evaluating drug and vaccine efficacy, for preventing epidemics, and determining agents of bioterrorism. Current diagnostic methods are either cumbersome, time-consuming, or have limited sensitivity. This example describes a nanofabrication technique to create novel SERS substrates that can be used to rapidly detect the Raman viral nucleic acid spectra of RNA and DNA viruses. Monoclonal antibodies reactive for individual RNA or DNA viruses were conjugated to these substrates, and it was demonstrated that low-levels of virus can be captured and unique SERS virus nucleic acid spectra generated for individual viruses. These SERS virus spectra provide a unique "molecular fingerprint" of individual viruses, and can be rapidly and sensitively used to detect clinically important respiratory viruses such as respiratory syncytial virus, adenovirus and parainfluenza virus type 3. These results show that SERS can differentiate RNA and DNA viral nucleic acid spectra, and indicate that a SERS-based viral biosensor would provide a framework for providing the molecular fingerprint of any virus.

This example further demonstrates a nanofabrication technique based on glancing angle vapor deposition that produces gold nanorod arrays that exhibit extremely high electromagnetic field enhancements when they are used as surface-enhanced Raman spectroscopy (SERS) substrates. Experiments were conducted to test whether the gold nanorods could be used to detect binding of virus to supported monoclonal antibodies via SERS. A self-assembled multilayer nanorod-antibody-virus immunoassay system was developed for binding of virus. In this system, thiol-derivatized IgG2a monoclonal antibodies were immobilized to the gold nanorod substrate. SERS spectra of the Ag nanorod/antibody complex were collected at 5 different spots on the substrate using the same spectrograph and under similar conditions: 785 nm excitation wavelength, 20 mW power, 10 s exposure time (data not shown).

The results of these experiments show that of the spectral features apparent in the IgG2a antibody spectrum (FIG. 12, top), the most intense band at ~1000 cm$^{-1}$ likely arises from the in-plane ring deformation mode of Phe in IgG. In the spectrum of the RSV+IgG complex (FIG. 12, bottom), prominent bands are observed in the 1400-1600 cm$^{-1}$ region, presumably due to selectively enhanced nucleic acid and/or side-chain vibrations. A more complete analysis of the SERS vibrational modes of these complexes is available. This example illustrates several of the advantages SERS possesses over other widely used biomedical detection methods. For example, no biochemical amplification (e.g. by PCR) of the viral nucleic acids is needed to enhance sensitivity. Also, no fluorescent reporter molecule is needed for SERS, and the narrow bandwidth of the SERS vibrations may allow identification of specific chemical constituents of the RSV virus, e.g. nucleic acids (G vs. U vs. A) or amino acids (Tyr vs. Trp vs. Phe).

Figure 8:
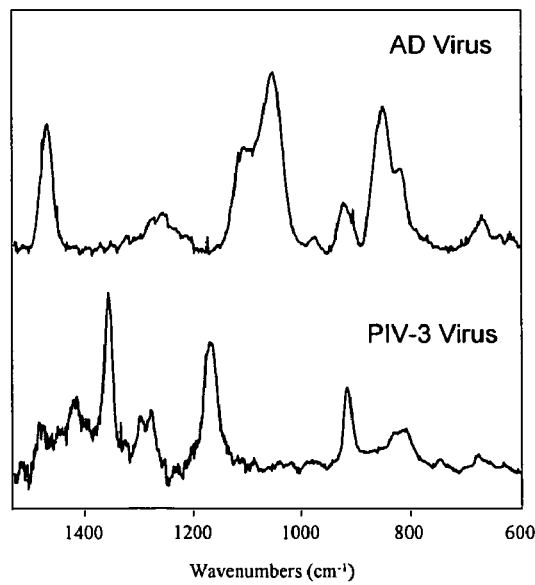
FIG. 8 illustrates a bulk phase Raman spectra of virus isolates of Adenovirus (AD) and Parainfluenza Virus (PIV-3).

In addition to the data showing that Raman spectroscopy may be used for RSV identification, bulk Raman spectra has been acquired for other viruses. FIG. 8 shows the Raman spectra of two additional virus in the region 1500-600 cm$^{-1}$. The spectra of both parainfluenza virus (PIV-3) and adenovirus (AD) are presented. PIV-3 is a filamentous virus with a single-stranded RNA genome while AD is an icosahedral virus with no membrane envelope and a double-stranded DNA genome. FIG. 8 shows that the bulk phase Raman spectra of these two respiratory viruses are significantly different and idiosyncratic. Based on these spectra, Raman marker bands have been identified that distinguish nucleoside conformations, base hydrogen bonding, DNA packing and stacking interactions. Different virions were able to be distinguished on the basis of their Raman band positions and intensities.

These results indicate that novel SERS substrates can be used to amplify the sensitivity of SERS as a diagnostic tool to detect the Raman spectra of extremely low levels of virus, as well as provide structural and quantitative information about the virus. The assay is rapid, ultra-sensitive, and does not require virus manipulation to achieve results. SERS spectroscopy can be used to develop molecular fingerprints of RNA and DNA viruses, to detect strain differences, and gene deletions or insertions.

Example 3

Experimental Method

The concentrations of the prepared virus samples in Dulbecco's Modified Eagle Medium (DMEM) were $10^7$ plaque forming units (pfus)/mL for HIV, $10^5$ TCID[50]/mL for Rhinovirus and $10^6$ TCID[50]/mL for the Adenovirus. After preparation, the virus samples were stored at −80° C. until the day of the experiment. The samples were thawed for about 5 minutes and an Eppendorf pipette was used to withdraw about 0.5 μL from the sample vial which was then allowed to spread onto the silver nanorod substrate corresponding to about 5000 plaque forming units (pfus) of HIV, about 350 pfus of Adenovirus and about 35 pfus of Rhinovirus. The virus droplet was allowed to dry and bind to the silver surface for ~1 hour prior to the Raman experiment.

Surface Enhanced Raman spectra were acquired using a Kaiser Optical Systems confocal Raman microscope (Kaiser Optical Systems Incorporated, Ann Arbor, Mich.) equipped with a liquid nitrogen cooled Charge Coupled Device (CCD) camera (Princeton, Instruments, Trenton, N.J.). The spectrograph used was a Holospec f/1.8-NIR spectrometer equipped with a HoloPlex grating that simultaneously measures the range of 100 to 3450 $cm^{-1}$ at an excitation wavelength of 785 nm illumination supplied by a Invictus Diode Laser (Kaiser Optical Systems Incorporated, Ann Arbor, Mich.). The spectra were collected using a 10× objective with ~20 mW of 785 nm light shining on the sample. SERS spectra were collected at different spots on the sample with collection times between 10 s-30 s.

All spectra were collected using the Holograms 4.0 software supplied by the manufacturer. Post processing of the collected spectra was performed using GRAMS32/AI spectral software package (Galactic Industries, Nashua, N.H.). Center of Gravity calculations were made using a GRAMS32 based program written in our laboratory (R. A. Dluhy, unpublished). All spectra were baseline corrected for clarity.

Figure 9:
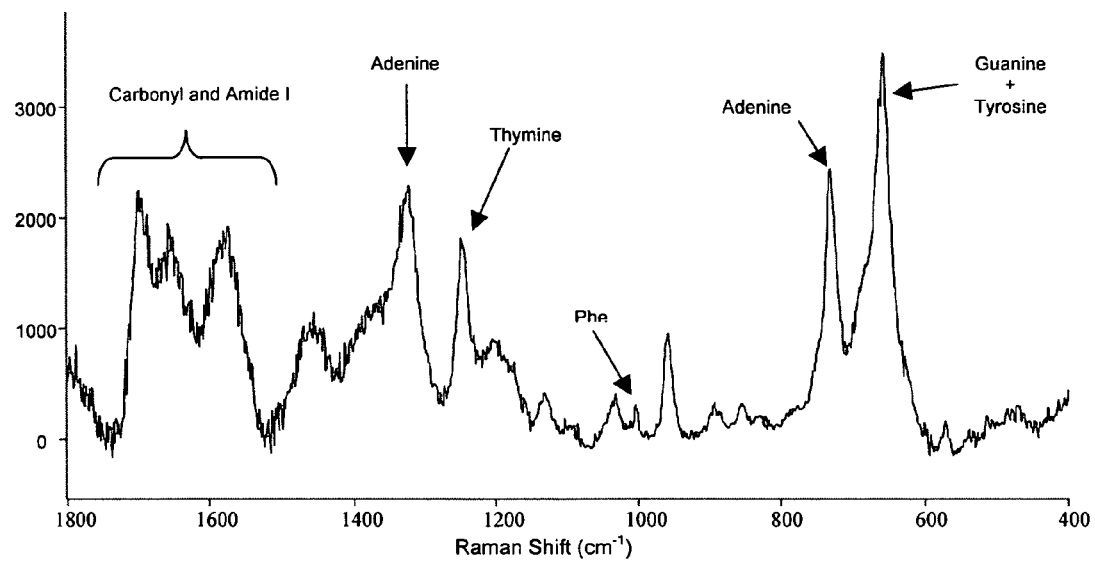
FIG. 9 illustrates a SERS spectrum of Adenovirus.
Figure 10:
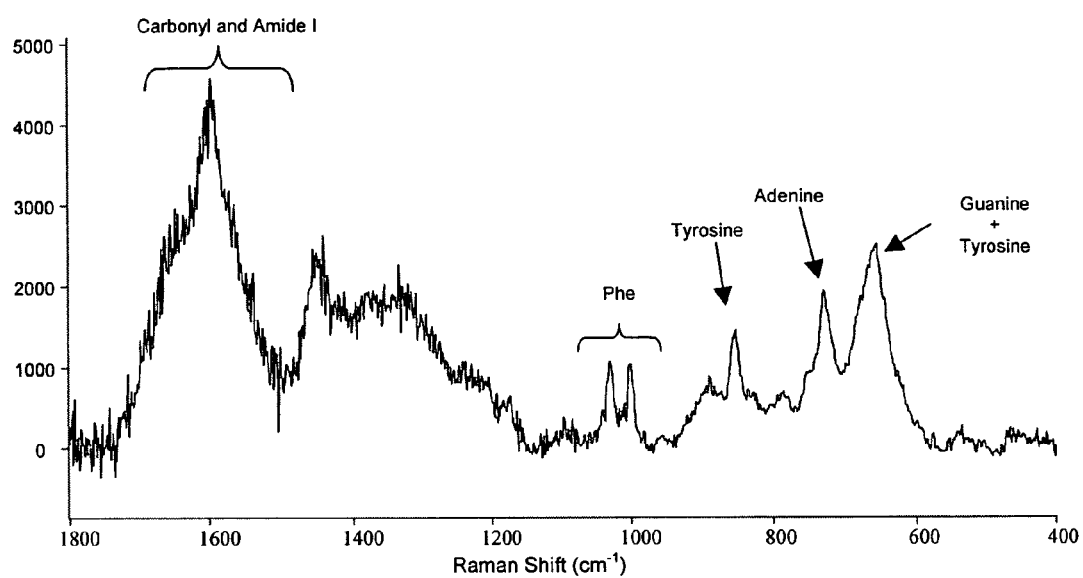
FIG. 10 illustrates a SERS spectrum of Rhinovirus.
Figure 11:
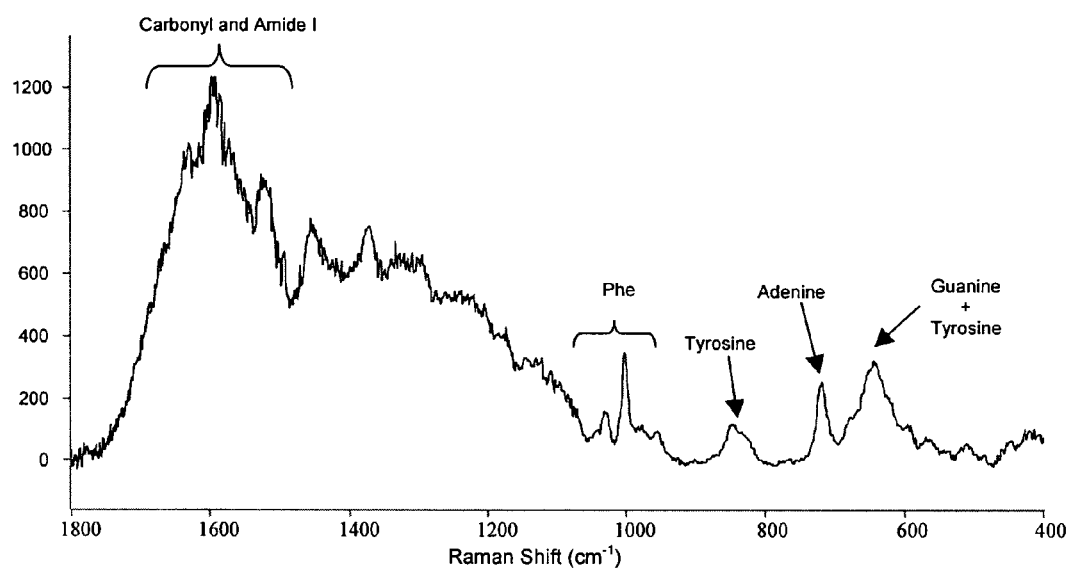
FIG. 11 illustrates a SERS spectrum of Human Immunodeficiency Virus (HIV).

Results:

Adenovirus, belonging to the Adenoviridiae family of viruses, is about 80 nm in diameter with an icosahedral core and contains double stranded DNA within the core. Rhinovirus belongs to the Picornaviridae family, is about 30 nm in diameter and the core has a single stranded RNA genome. Human Immunodeficiency Virus (HIV) belongs to the Retroviridae family, is approximately 120 nm in diameter and has a single stranded RNA genome contained within a lipid-bilayer envelope. Spectra collected from different spots on the SERS substrate did not differ greatly and the displayed spectra are representative of the entire data set. The SERS spectra of the Adenovirus, Rhinovirus and HIV specimens are shown in FIGS. 9-11, respectively, and the corresponding band assignments are shown in Tables 1-3.

Raman bands can be assigned to chemical constituents such as DNA, RNA, phenylalanine, tyrosine and proteins for all the spectra. The most prominent spectral features observed in the spectra are at 654 $cm^{-1}$, 730 $cm^{-1}$, 1247 $cm^{-1}$ and 1326 $cm^{-1}$ corresponding to Guanine, the Adenine ring vibration, thymine and Adenine respectively. The Raman bands between 1580 $cm^{-1}$ and 1700 $cm^{-1}$ can be attributed to carbonyl groups on the amino acid side chains and the Amide I vibration while the spectral region near 1000 $cm^{-1}$ has bands due to Phenylalanine (1001 $cm^{-1}$ and 1030 $cm^{-1}$).

TABLE 1

Adenovirus

| Raman Shift ($cm^{-1}$) | Band Assignments |
| --- | --- |
| 653 | Tyrosine + Guanine (A – DNA) |
| 684 | Guanine (disordered or B – DNA) |
| 730 | Adenine Ring Vibration |
| 855 | Tyrosine |
| 957 | Protein (C – C) or DNA backbone |
| 1001 | Phenylalanine |
| 1031 | Phenylalanine |
| 1240 | Thymine (A – DNA) |
| 1323 | Adenine (B – DNA) |
| 1371 | Tryptophan + Phenylalanine |
| 1454 | $CH_2$ deformation |
| 1585 | Carbonyl |
| 1625 | Carbonyl, Amide I |

TABLE 2

Rhinovirus

| Raman Shift ($cm^{-1}$) | Band Assignments |
| --- | --- |
| 660 | Tyrosine + Thymine + Guanine |
| 730 | Adenine Ring Vibration |
| 1001 | Phenylalanine |
| 1031 | Phenylalanine |
| 1323 | Adenine |
| 1369 | Tryptophan + Phenylalanine |
| 1449 | $CH_2$ deformation |
| 1597 | Tryptophan + Phenylalanine + Adenine + Guanine |
| 1650 | Amide I |

TABLE 3

HIV

| Raman Shift ($cm^{-1}$) | Band Assignments |
| --- | --- |
| 652 | Tyrosine + Guanine |
| 685 | Guanine |
| 730 | Adenine Ring Vibration |
| 1001 | Phenylalanine |
| 1031 | Phenylalanine |
| 1096 | RNA Backbone |
| 1137 | Protein (C – N) |
| 1371 | Tryptophan + Phenylalanine |
| 1454 | $CH_2$ deformation |
| 1600 | Carbonyl |

Example 4

Virus Detection Using Ag Nanorod-Based SERS

The present examples present experiments demonstrating the use of embodiments of the SERS system of the present disclosure (Ag nanorod substrates) as a rapid and sensitive method for virus detection.

Virus Preparation Methods

Four human viruses were analyzed, including respiratory syncytial virus (RSV) strain A2, rhinovirus type 4/strain 16/60 (rhino), adenovirus type 6/tonsil strain 99 (Ad), and a CXCR4-tropic strain of human immunodeficiency virus (HIV). RSV, Ad and rhino viruses were propagated using Vero cells maintained in Dulbecco's Modified Eagles Medium (DMEM; GIBCO BRL laboratories, Grand Island, N.Y.) supplemented with 2% heat-inactivated (56° C.) FBS (Hyclone Laboratories, Salt Lake City, Utah) until detectable cytopathic effect. The control for these studies was uninfected Vero cell lysate cleared of cell debris by centrifugation (4000×g, 15 min, 4° C.). RSV, Ad and rhino viruses were harvested in serum-free DMEM following by two freeze-thaws (−70° C./4° C.), after which the contents were collected and centrifuged at 4000×g for 15 min at 4° C. The virus titers were similar and ranged between $5 \times 10^6$-$1 \times 10^7$ pfu/ml determined by an immunostaining plaque assay as previously described (R. A. Tripp, D. Moore, L. Jones, W. Sullender, J. Winter and L. J. Anderson, "Respiratory syncytial virus G and/or SH protein alters Th1 cytokines, natural killer cells, and neutrophils responding to pulmonary infection in BALB/c mice", *J. Virol.* 1999, 73, 7099-7107, which is hereby incorporated by reference herein).

RSV was purified as previously described (A. Mbiguino and J. Menezes, "Purification of human respiratory syncytial virus—superiority of sucrose gradient over percoll, renografin, and metrizamide gradients", *J. Virol. Meth.* 1991, 31, 161-170. and B. F. Fernie and J. L. Gerin, "The stabilization and purification of respiratory syncytial virus using $MgSO_4$", *Virology* 1980, 106, 141-144, which is hereby incorporated by reference herein). Virus purification was performed using a sucrose cushion to allow comparison of spectral bands in the SERS spectrum of RSV infected cell lysate to virus alone. RSV-infected cell lysate was layered onto a 77% sucrose solution in MHN buffer (0.1M magnesium sulfate, 0.15M sodium chloride, 0.05M HEPES) and centrifuged at 27,000×g for 1.5 hours at 4° C. The interphase was collected, diluted with 2 volumes of MHN buffer and layered onto a step gradient of 77% sucrose in MHN buffer and 33% sucrose in MHN buffer and centrifuged at 100,000×g for 1 hour at 4° C. The interphase on the top layer containing purified RSV was collected and dialyzed against PBS. HIV was propagated by infecting human white blood cells (WBCs) previously stimulated with phytohemmaglutinin (PHA, Sigma) as previously described (J. S. McDougal, S. P. Cort, M. S. Kennedy, C. D. Cabridilla, P. M. Feorino, D. P. Francis, D. Hicks, V. S. Kalyanaraman and L. S. Martin, "Immunoassay for the detection and quantitation of infectious human retrovirus, lymphadenopathy-associated virus (LAV)", *J. Immunol. Methods* 1985, 76, 171-183, which is hereby incorporated by reference herein), and viruses titers assayed by ID50 to determine the number of infectious particles per mL. Virus was inactivated by treatment with 4% paraformaldehyde at room temperature for 3 hours. The concentrations of the prepared virus samples in Dulbecco's Modified Eagle Medium (DMEM) were $10^7$ pfu/mL for HIV, $10^5$ TCID[50]/mL for Rhinovirus, $10^6$ TCID [50]/mL for the Adenovirus, and $10^3$ pfu/mL for RSV.

SERS Procedures

SERS spectra were acquired using a near-IR confocal Raman microscope (Hololab Series 5000, Kaiser Optical Systems, Inc., Ann Arbor, Mich.). A fiber-optic interfaced 785 nm near-IR diode laser (Invictus, Kaiser Optical) was used as the laser source. The spectrograph was a Kaiser Optical Holospec f/1.8-NIR equipped with a $LN_2$-cooled CCD camera (1024EHRB, Princeton Instruments, Trenton, N.J.). The laser power at the sample was ~15 mW with spectral collection times ranging between 30 s-50 s. SERS spectra were collected from multiple spots across the substrate and from multiple substrates. Approximately 0.5-1.0 μL of intact virus was applied to the SERS substrate and allowed to bind for 1 hour at room temperature prior to spectrum acquisition.

SERS can Detect RSV Bound to a Surface

The present example demonstrates that Ag nanorods prepared as described in Example 4, hereinabove can be used to detect binding of RSV to supported antibodies via SERS. A self-assembled multilayer nanorod-antibody-virus immunoassay was developed for binding of RSV. In this system, thiol-derivatized IgG2a monoclonal antibodies were immobilized to the Ag nanorod substrate. After 1 hour the excess unreacted antibody was washed off with saline solution. SERS spectra of the Ag nanorod/antibody complex were collected at 5 different spots on the substrate using the same spectrograph and similar spectral data collection conditions to those described above: 785 nm excitation wavelength, ~20 mW power, 10 s exposure time.

Virus binding was accomplished by exposing the IgG-coated Ag nanorod to a solution of RSV virus. After 1 hour incubation, the excess RSV on the surface of the substrate was removed. SERS spectra of the RSV-IgG complex on the Ag nanorods were then collected using the same spectral conditions as before.

Figure 12:
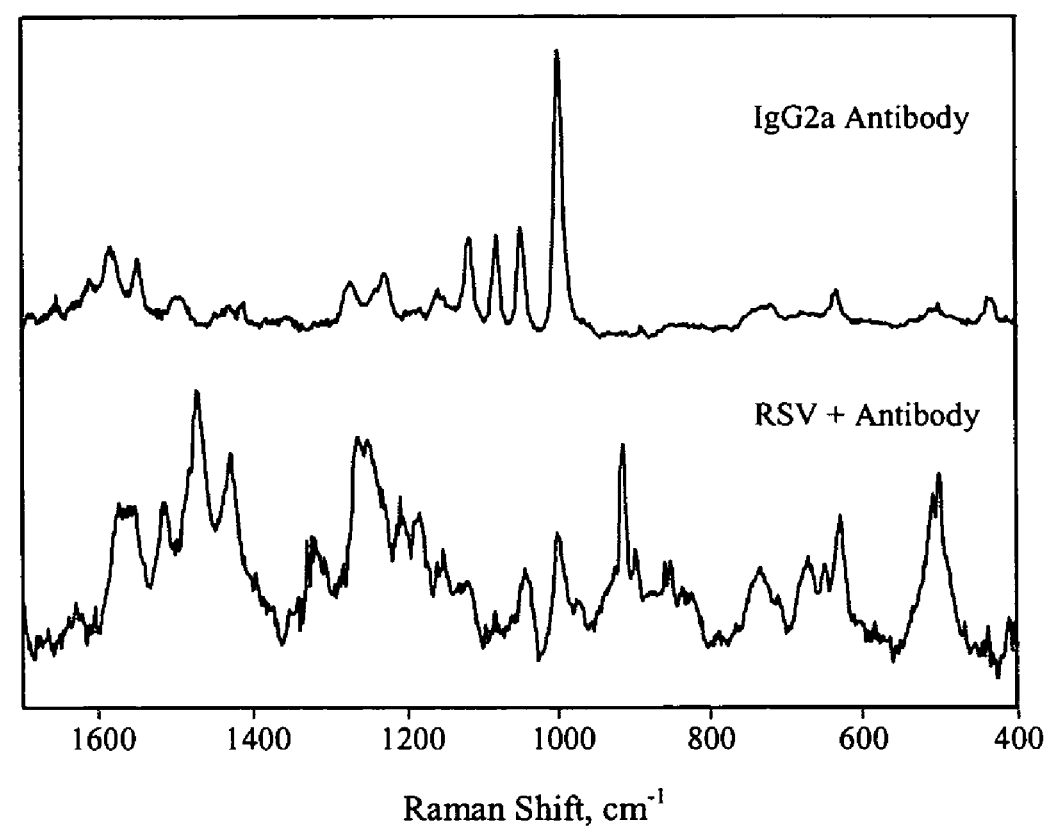

The results of these experiments are shown in FIG. 12. Of the spectral features apparent in the IgG2a antibody spectrum (FIG. 12, top), the most intense band at ~1000 $cm^{-1}$ likely arises from the in-plane ring deformation mode of Phe in IgG. In the spectrum of the RSV+IgG complex (FIG. 12, bottom), prominent bands are observed in the 1400-1600 $cm^{-1}$ region, presumably due to selectively enhanced nucleic acid and/or side-chain vibrations, although the amide III protein mode at ~1260 $cm^{-1}$ may be observed in both the IgG and RSV+IgG spectra.

FIG. 12 illustrates several of the advantages SERS possesses over other widely used biomedical spectroscopic tools such as fluorescence. For example, no biochemical amplification (e.g. by PCR) of the viral nucleic acids is needed to enhance sensitivity. Also, no fluorescent reporter molecule is needed for SERS, and the narrow bandwidth of the SERS vibrations may allow identification of specific chemical constituents of the RSV virus, e.g. nucleic acids (G vs. U vs. A) or amino acids (Tyr vs. Trp vs. Phe).

SERS can Distinguish Between Different Viruses Based on their Raman Spectra

The present example also demonstrates that the SERS system of the present disclosure can be used to differentiate between different viruses, including both RNA and DNA viruses by contacting a virus sample directly with nanorod array of the SERS substrate without functionalizing the nanorods with a virus-specific binding agent. Instead, different viruses can be distinguished based on their unique SERS spectra. The baseline corrected enhanced Raman spectra of Ad, rhino and HIV viruses are shown in FIG. 13. The Ad SERS spectrum is characterized by strong bands due to nucleic acid bases at 650 $cm^{-1}$ (G), 731 $cm^{-1}$ (A), 1325 $cm^{-1}$ (A) and 1248 $cm^{-1}$ (G). The 650 $cm^{-1}$ band may also have contributions due to Tyr. The Raman lines at 1003 $cm^{-1}$ and 1033 $cm^{-1}$ have been assigned to the symmetric ring breathing mode and the in-plane C—H bending mode of Phe, respectively, while the bands at 1457 $cm^{-1}$, 1576 $cm^{-1}$, and 1655 $cm^{-1}$ can be attributed to the $CH_2$ deformation mode of proteins, the carboxylate stretching vibration ($v_a$ $COO^-$) of Trp, and the amide I vibration of peptide groups, respectively. A notable characteristic of the Ad SERS spectrum is the relative intensity of the bands associated with the nucleic acids indicating direct binding to the silver substrate. The strong band at 731 $cm^{-1}$ has been assigned to denatured DNA caused by its interaction with the silver SERS substrate.

In the SERS spectrum for rhinovirus, the major Raman bands are present at 656 $cm^{-1}$ (G), 729 $cm^{-1}$ (A), 853 $cm^{-1}$ (Tyr), 1002 $cm^{-1}$ and 1030 $cm^{-1}$ (Phe), 1448 $cm^{-1}$ ($CH_2$ deformation), and 1597 $cm^{-1}$ ($v_a$ $COO^-$ in Trp). On comparison with the Ad SERS spectrum, a shift in the frequency of the guanine band is apparent. Other differences that distinguish the SERS spectrum of rhino from Ad are the relative intensity of the nucleic acid bands compared to the other bands in the spectrum and the absence of strong nucleic acid bands at higher wave numbers. For the HIV SERS spectrum, the Raman bands at 643 cm$^{-1}$, 719 cm$^{-1}$, 848 cm$^{-1}$, 1002 cm$^{-1}$, 1371 cm$^{-1}$, 1454 cm$^{-1}$, and 1523 cm$^{-1}$ can be assigned to G, A, Try, Phe, the $v_s$ COO$^-$ stretch of Trp, the CH$_2$ deformation band, and the $v_a$ COO$^-$ of Trp, respectively. Notable differences include the spectral positions of the guanine band (643 cm$^{-1}$) and the adenine band (719 cm$^{-1}$) that are shifted with respect to the bands for the Ad and rhino spectra, and the presence of a band at 1523 cm$^{-1}$ in the HIV spectrum that is absent in the spectra of the other two viruses. These unique spectral features provide distinguishing spectral characteristics for each of the viruses examined.

These results, along with the spectra of RSV in FIG. 12, demonstrate that SERS can be used to establish molecular fingerprints of several important human respiratory viruses, as well as HIV. These results highlight the use of SERS as a detection method for important pathogenic viruses central to human health care.

SERS can Detect Viruses in Biological Media

Figure 14:
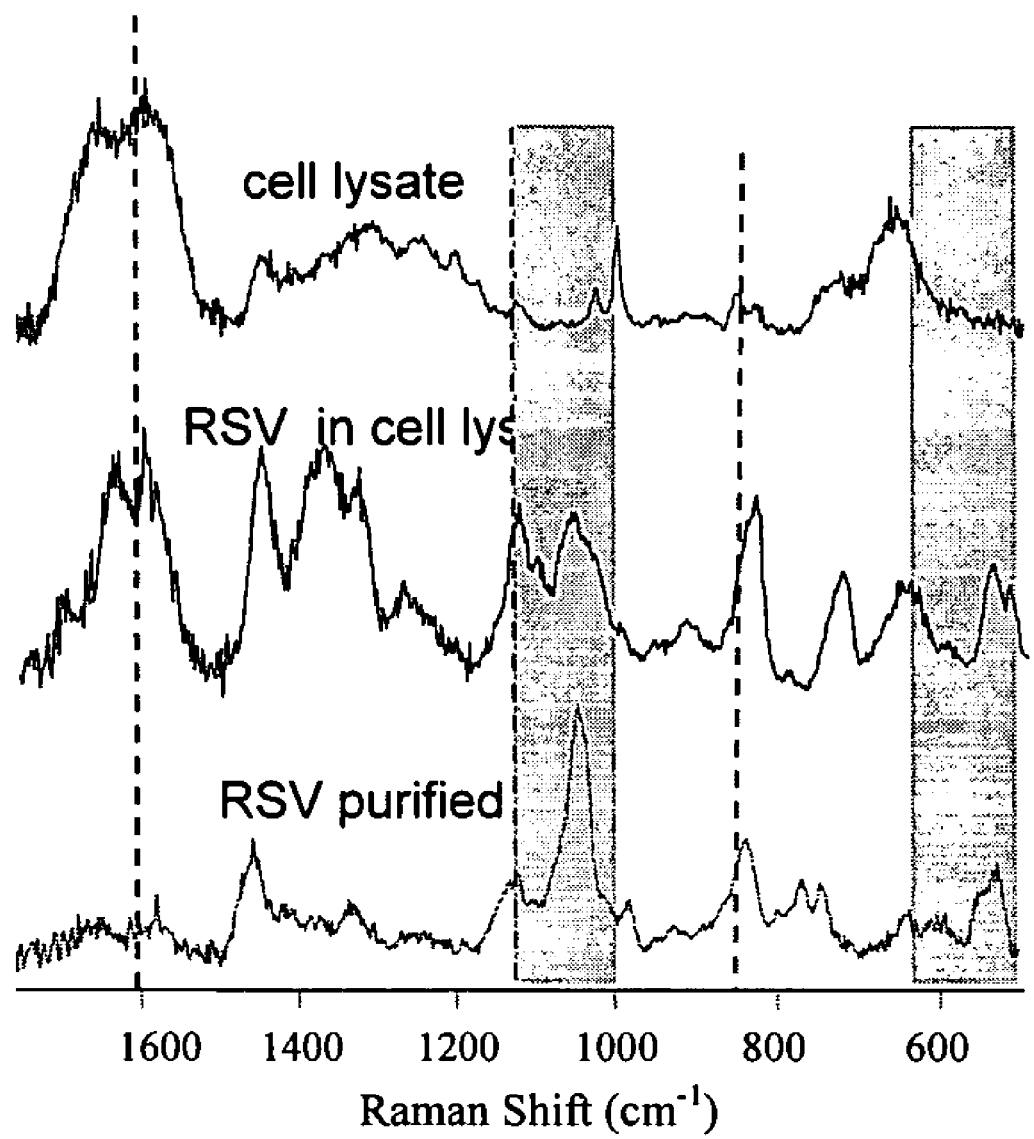
FIG. 14 illustrates a SERS spectra of Vero cell lysate before (top) and after (middle) infection with RSV, as compared to the SERS spectrum of purified RSV (bottom).
Figure 15:
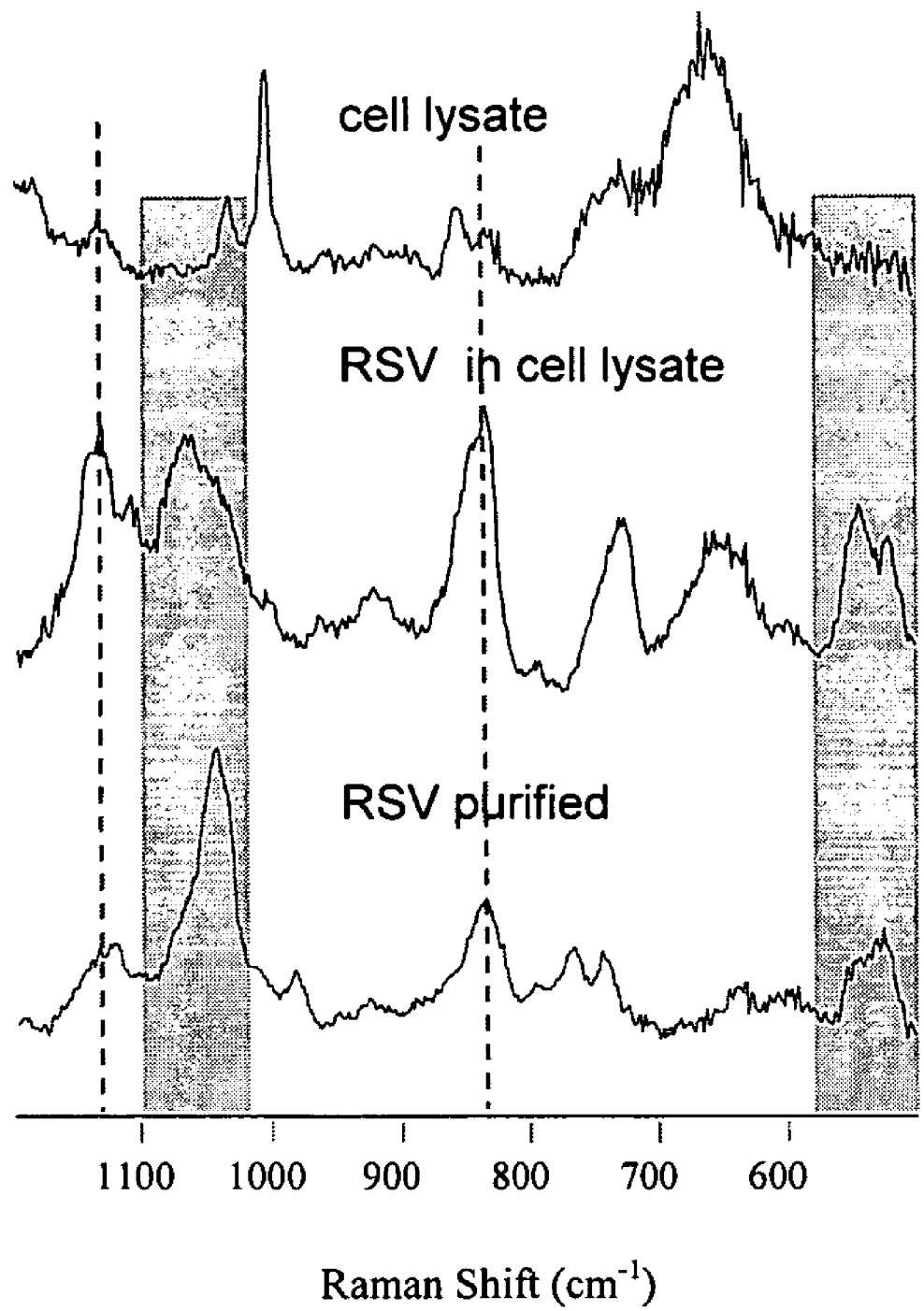
FIG. 15 illustrates a comparison of the SERS spectra of Vero cell lysate before (top) and after (middle) infection with RSV and a purified RSV composition (bottom).

The present example also demonstrates that Ag nanorod-based SERS is not only sensitive to purified virus, but also is able to sense the presence of virus after infection of biological media without the use of a virus-specific binding agent to functionalize the nanorod array. To demonstrate this, the SERS spectra of uninfected Vero cell lysate, RSV-infected cell lysate, and purified RSV were compared (FIGS. 14 and 15). The results show that major Raman bands can be assigned to different constituents of the cell lysate and the virus, such as nucleic acids, proteins, protein secondary structure units and amino acid residues present in the side chains and the backbone. However, significantly, it was shown that vibrational modes due to the virus could be unambiguously identified in the SERS spectrum of the Vero cell lysate after infection.

In the SERS spectrum of purified RSV, the bands at 527 cm$^{-1}$ and 546 cm$^{-1}$ can be assigned to a disulfide stretching mode. This region is identified with the shaded bands in FIGS. 14 and 15. The strong band at 837 cm$^{-1}$ (identified with a dashed line in FIGS. 14 and 15) corresponds to Tyr. An important feature in the RSV SERS spectrum is a strong band at 1044 cm$^{-1}$ (identified with the shaded band in FIGS. 14 and 15) that has been assigned to the C-N stretching vibration in previous SERS studies. Since RSV has spike-like glycoprotein projections on the membrane envelope including three different glycoproteins (e.g., F, G and SH) it is believed that the virus binds to the Ag nanorod SERS substrate through an amino group giving rise to a strong C-N stretching mode. The Raman band at 1456 cm$^{-1}$ can be assigned to the CH$_2$ deformation vibration arising from the proteins or the lipids in the membrane. In the case of the SERS spectrum of the uninfected Vero cell lysate, the bands at 658 cm$^{-1}$ and 730 cm$^{-1}$ can be assigned to the nucleic acids guanine and adenine, respectively, while the Raman bands observed above 1500 cm$^{-1}$ in FIG. 14 (identified the left-hand dashed line) can be assigned to amino acids and Amide I and II vibrations.

The SERS spectrum of the RSV-infected cell lysate shows several bands that are also observed in the uninfected cell lysate spectrum and can be attributed to the constituents of cell debris (FIGS. 14 and 15). However, strong bands can be observed at 1066 cm$^{-1}$ (C-N stretch), 835 cm$^{-1}$ (Tyr) and a doublet at 545 cm$^{-1}$ and 523 cm$^{-1}$ (S-S stretch) that are present in the SERS spectrum of the RSV-infected cell lysate, but not in the spectrum of the uninfected cell lysate. The appearance of these bands clearly indicates the presence of RSV in the biological medium that is the cell lysate. The small difference in the wavenumber position of the C-N stretching mode between the purified RSV and RSV infected cell lysate is most likely due to the interaction between the RSV and the Vero cells.

In these examples, small spectral bands were observed on the blank SERS substrate that have been attributed to carbonaceous material adsorbing onto the substrate during the fabrication of the SERS substrate and its storage under ambient conditions. However, these bands (data not shown) were found to remain unchanged throughout the experimentation, and exposure to laser radiation did not affect their position or intensities. Except for minor differences in relative band widths and intensities, the SERS virus spectra collected from multiple spots on the Ag nanorod substrate were substantially identical.

Example 5

SERS can Detect Different Strains within a Single Virus Type

Figure 16:
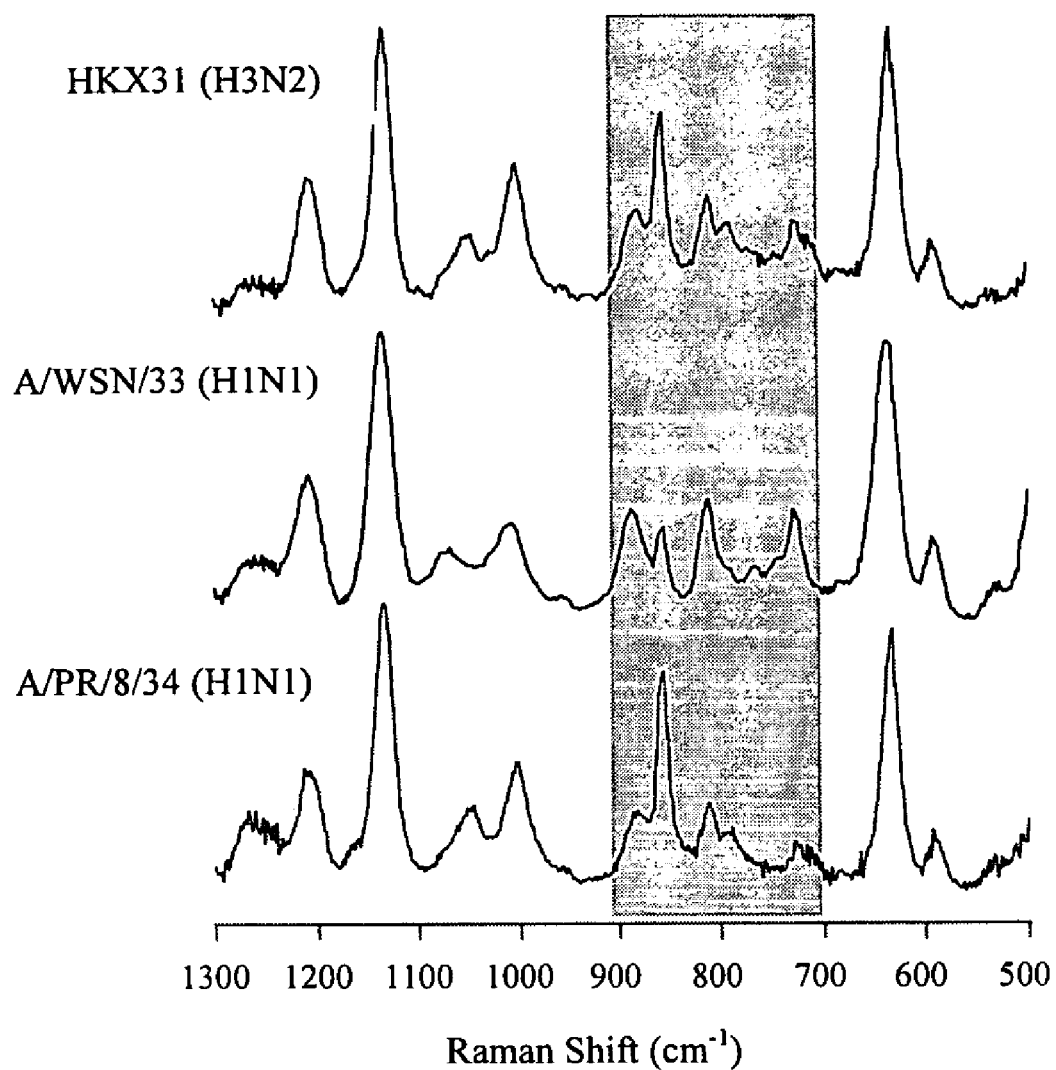
FIG. 16 illustrates a comparison of the SERS spectra of three different strains of the influenza virus using the Ag nanorod SERS substrates of the present disclosure. Strain HKX31 (H3N2) is the top, A/WSN/33 (H1N1) is the middle, and A/PR/8/34 (H1N1) is the bottom spectrum.

The influenza (flu) viruses, HKX-31 (H3N2), A/WSN/33 (H1N1) and A/PR/8/34 (H1N1) belonging to the strain A, were analyzed using SERS as described above by contacting samples containing the virus (prepared as set forth in Example 4 above) directly with the Ag nanorod surface of the SERS substrate (without a binding agent). The corresponding baseline corrected spectra (1300 cm$^{-1}$-500 cm$^{-1}$) are shown in FIG. 16. Influenza A is an enveloped virus with two distinct glycoproteins on the surface (e.g., hemagglutinin and neuraminidase) that are embedded in a lipid bilayer. These two proteins are responsible for all of the known different subtypes of influenza, with 14 different known hemagglutinins and 9 different known neuraminidases. As can be seen in FIG. 16, the SERS spectra of the three strains within a single virus type (FIG. 16) are more similar than are the SERS spectra between virus types. The main bands in the spectra of the flu strains in FIG. 16 appear at 1206 cm$^{-1}$ (Tyr), 1130 cm$^{-1}$ v(C-C), 1047 cm$^{-1}$ v(C-N), 1003 cm$^{-1}$ (Phe), 885 cm$^{-1}$ (Gly), 635 cm$^{-1}$ (Tyr), and 592 cm$^{-1}$ (Gly). These vibrations can be assigned to amino acid, protein or nucleic acid molecules, as indicated. The band at 812 cm$^{-1}$ has been assigned to the phosphate backbone stretch of the RNA on previous bulk Raman studies on viruses. The flu viruses are known to contain a single stranded RNA within their core. In the case of the A/WSN sample, the band at 1071 cm$^{-1}$ is slightly shifted from 1047 cm$^{-1}$ as compared to the other two samples. This could be due to a difference in the nature of binding of the surface proteins on the surface of this particular virus.

Although they appear somewhat similar, small differences in the flu strain Raman spectra in FIG. 16 are apparent that may allow the individual identification flu strains in a complex mixture. For example, the spectral regions between 900-700 cm$^{-1}$ (highlighted in FIG. 16) show intensity differences as well as frequency shifts in the spectra of the three strains.

Example 6

SERS can Detect Different Strains within a Single Virus Type

Figure 17:
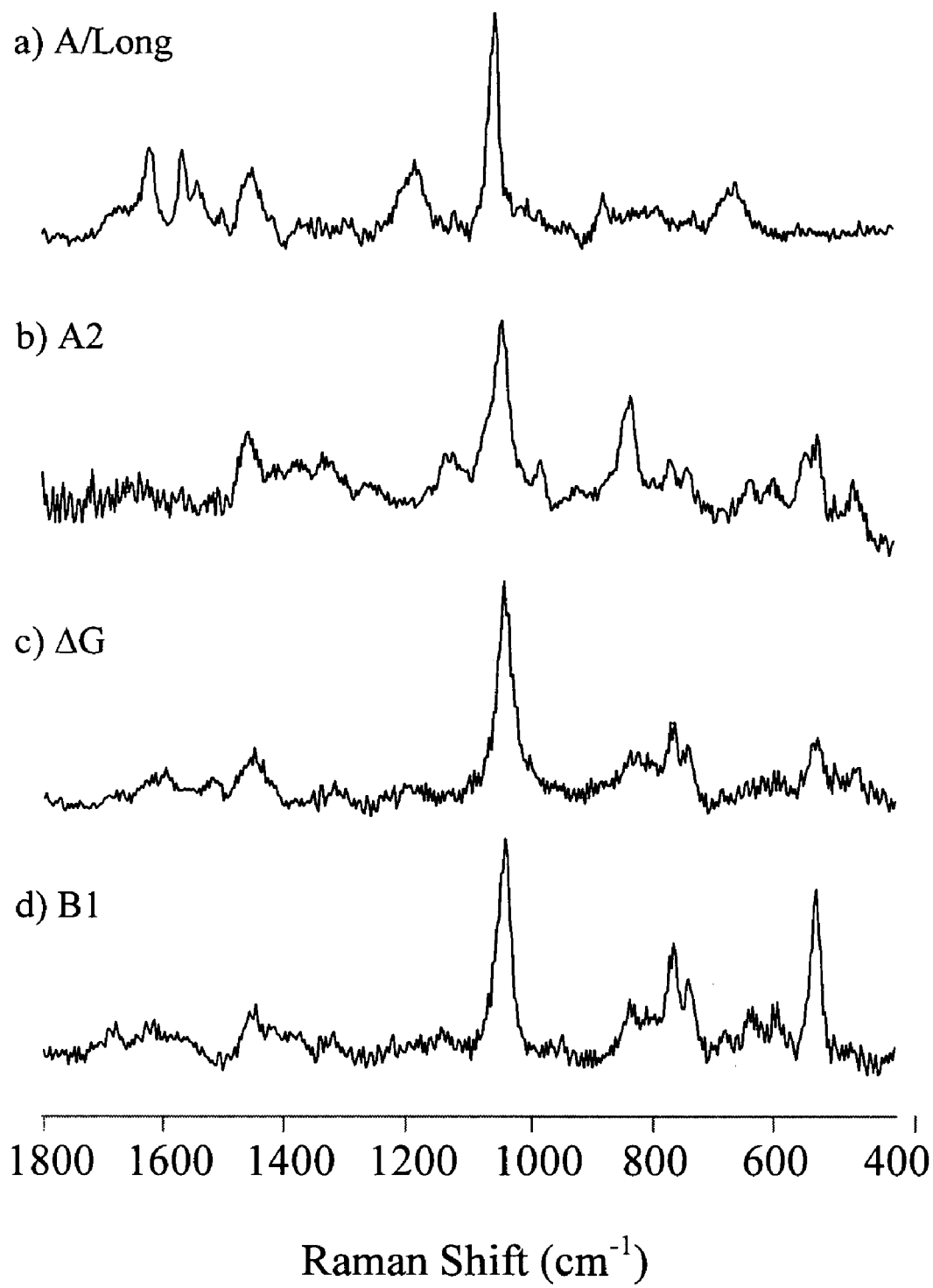
FIG. 17 illustrates a comparison of SERS spectra of RSV viruses: a) strain A/Long (A/Long), b) strain A2 (A2), c), strain A2 with a G gene deletion ($\Delta G$), and d) strain B1 (B1). The main band in the spectrum that is due to the C-N stretch occurs at 1055 $cm^{-1}$.
Figure 18:
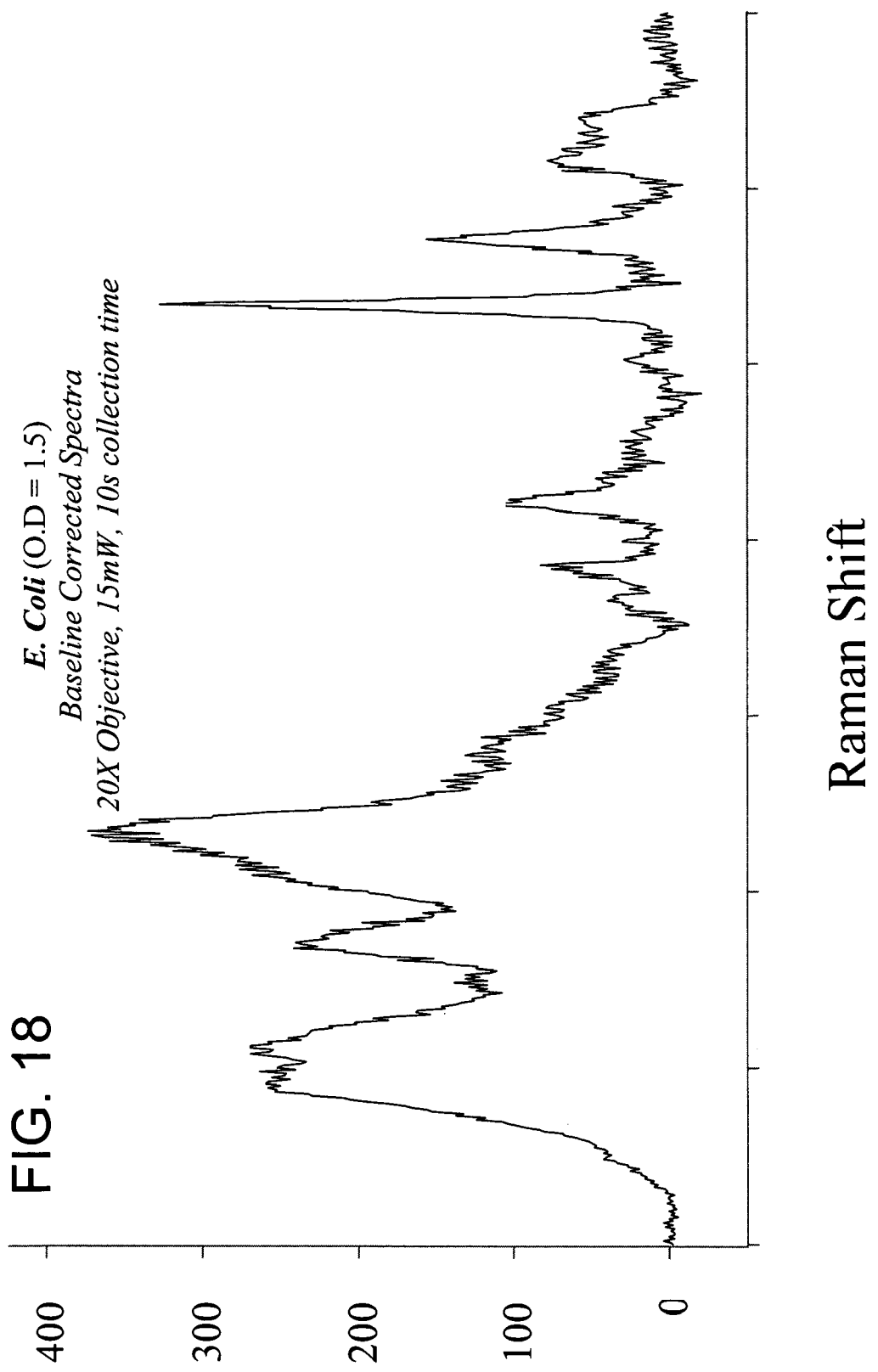
FIG. 18 illustrates a representative SERS spectrum of *E. Coli*.
Figure 19:
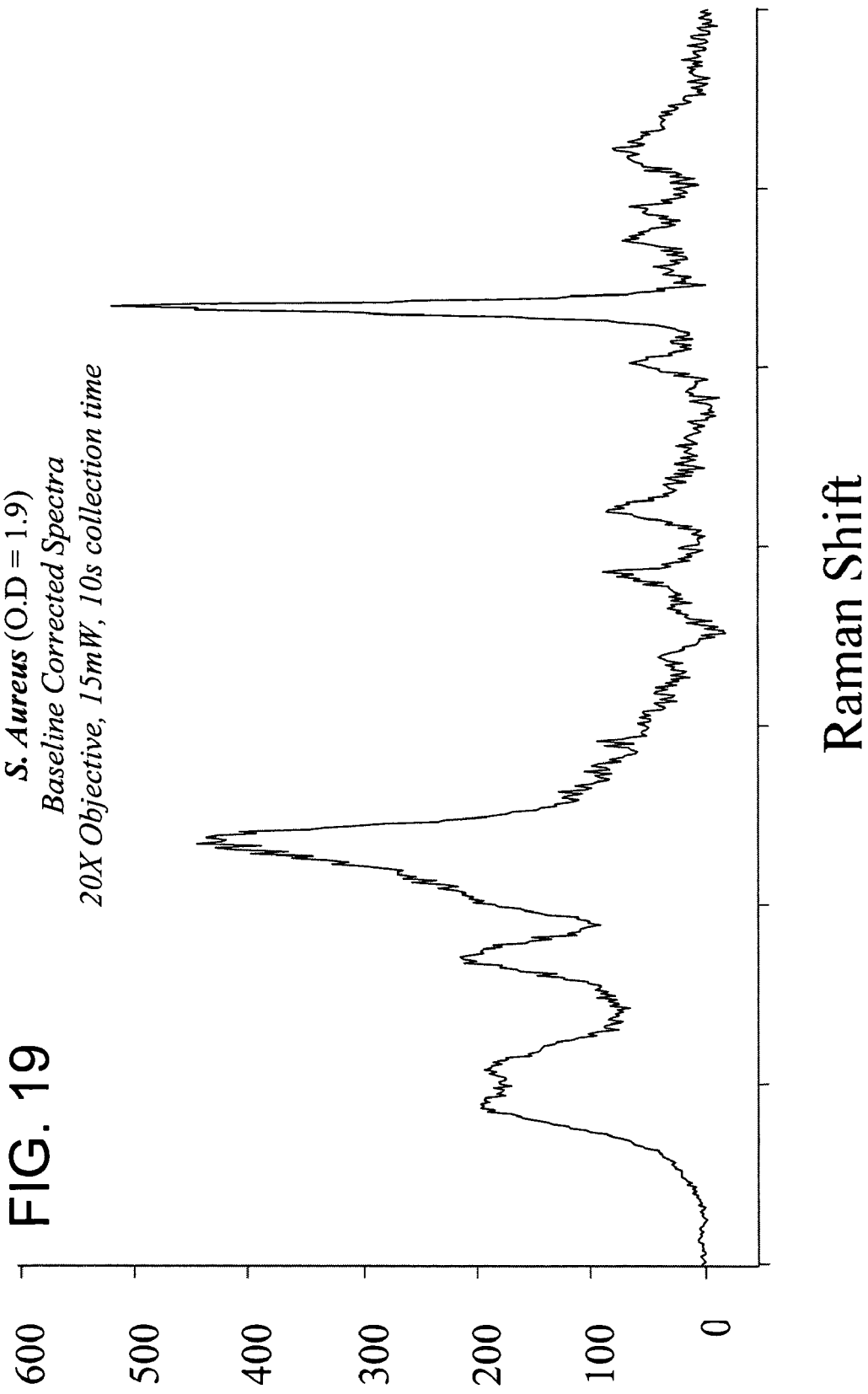
FIG. 19 illustrates a representative SERS spectrum of *S. Aureus*.
Figure 20:
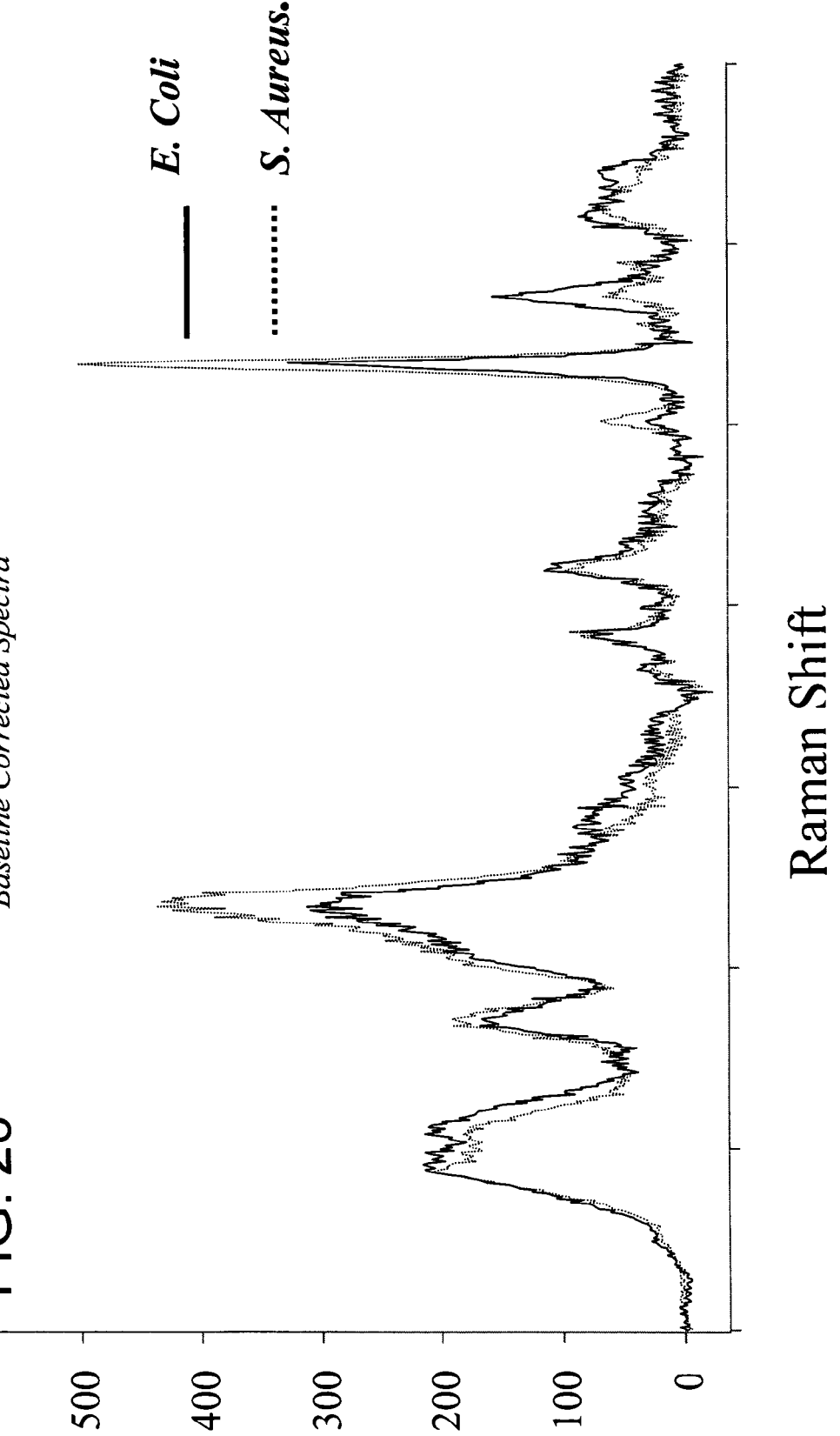
FIG. 20 illustrates a representative SERS spectrum comparison of the *E. Coli* and *S. Aureus*. It should noted that embodiments of the present disclosure can distinguish between *E. Coli* and *S. Aureus* based on at least the following: (1) The ratio of the Adenine (734 cm−1) and Guanine (685 cm−1) band intensities A/G for *E. Coli* is ~2.1 while for *S. Aureus* ~8.5 (Based on ratio calculated for 6 different spectra on a single substrate); and (2) Region between 500 cm−1-600 cm−1.

Different strains of RSV were analyzed by SERS to detect differences in their Raman spectral fingerprints (FIG. 17).

The spectra are representative of multiple spots on three different SERS substrates. The RSV strains examined were RSV A strains A/Long (a), A2 (b), ΔG (c) and the RSV B strain, B1 (d). Based on the findings for influenza virus strains (FIG. 16), and the observation that primary Raman bands arise due to surface proteins and nucleic acids, minor but notable differences were expected in the Raman spectra for RSV strains. The SERS spectrum of A/Long (FIG. 17, a) differed from the other RSV spectra in band frequency. The main band in the spectrum that is due to the C-N stretch occurs at 1055 cm$^{-1}$ compared to 1042 cm$^{-1}$-1045 cm$^{-1}$ for the other RSV viruses. Bands unique to A/Long are also observed at 877 cm$^{-1}$ and 663 cm$^{-1}$ while the band at 528 cm$^{-1}$ (present in the other spectra) is absent. Although not intending to be bound by theory, it is likely that the different spectrum observed for A/Long virus relates to the different nucleic acid composition and the proteins present on the viral envelope. There were also differences in the SERS spectra between RSV A strains and the B1 strain. The differences that distinguished the SERS A strain spectra from the SERS B strain spectrum include the relative intensities of the nucleic acid bands compared to the other bands in the spectrum. Importantly, SERS also has the ability to detect gene deletions in viruses. This is shown by the SERS spectra comparing the parental A2 strain (FIG. 17, b) to the RSV G protein gene mutant virus from which it was derived, ΔG (FIG. 17, c). Comparison of the spectra reveals differences in peak intensities of the Raman spectra between 700 cm$^{-1}$-900 cm$^{-1}$.

Discussion

The SERS spectra associated with the nanostructured metal substrate and analyte of interest provides rapid detailed fingerprint information about the molecular composition of the adsorbed biomaterial in a non-destructive manner. The technology and methodology to acquire and interpret biological SERS spectra is currently available and relatively easily applied. These results from these studies show that the SERS spectra of viruses can be used to rapidly distinguish between viruses, virus strains, and can detect gene deletions, thus serving as a rapid and reproducible means to molecularly fingerprint viruses. These results also suggest that is possible to use SERS to collect the spectra of various viruses and virus strains to develop a reference library of vibrational Raman fingerprints that can be used to rapidly and accurately identify viruses in very small (0.5-1.0 μL) volumes.

CONCLUSIONS

Compared to previous studies relying on bulk Raman analysis of viruses, the SERS studies shown here represent a dramatic biotechnological advancement allowing for more rapid observation of Raman spectra of extremely small amounts of analyte, particularly since the spectra can be obtained with greatly reduced data accumulation times and incident laser powers. The speed, specificity and relative ease of implementation of the SERS technique make it a very important alternative to current viral diagnostic tools and methodologies, and offers new virus detection means that are central to human health care.

Viruses.

The following human respiratory viruses were used in the analyses: respiratory syncytial virus (RSV) strain A2, RSV strain A/Long, RSV strain B1, recombinant wild type RSV strain A2 (6340), 6340 with a deletion of the G gene (AG). RSV viruses were propagated using Vero cells maintained in Dulbecco's Modified Eagles Medium (DMEM; GIBCO BRL laboratories, Grand Island, N.Y.) supplemented with 2% heat-inactivated (56° C.) FBS (Hyclone Laboratories, Salt Lake City, Utah). Upon detectable cytopathic effect, RSV viruses were harvested in serum-free DMEM following by two freeze-thaws (−70° C./4° C.), after which the contents were collected and centrifuged at 4000 g for 15 min at 4° C. The virus titers were similar and ranged between 5×10$^6$-1× 10$^7$ PFU/ml determined by immunostaining plaque assay as previously described above. The control for these studies was uninfected Vero cell lysate cleared of cell debris by centrifugation (4000 g, 15 min, 4° C.). As necessary, viruses were inactivated by 4% paraformaldehyde treatment at room temperature for 3 h hours.

Virus Purification.

RSV purification was done on a sucrose cushion to allow comparison of spectral bands in the SERS spectrum of RSV infected cell lysate to virus alone. The purification was done as previously described with slight modifications. Briefly, RSV-infected cell lysate was layered onto a 77% sucrose solution in MHN buffer (0.1M magnesium sulfate, 0.15M sodium chloride, 0.05M HEPES) and centrifuged at 27,000×g for 1.5 hours at 4 C. The interphase was collected, diluted with 2 volumes of MHN buffer and layered onto a step gradient of 77% sucrose in MHN buffer and 33% sucrose in MHN buffer and centrifuged at 100,000×g for 1 hour at 4° C. The interphase on the top layer containing purified RSV was collected and dialyzed against PBS. The concentrations of the purified virus samples were ~5×10$^8$ PFU/ml.

Example 7

SERS can Detect Different Types of Bacterium

SERS was used to analyze the Gram negative bacterium *Escherichia Coli* and the Gram positive bacterium, *Staphylococcus Aureus*. The bacterial cells were grown to an OD$_{600}$ of 1.5 for *E. Coli* and 1.9 in the case of the *S. Aureus*, washed five times with water and re-suspended in ~1 mL water. About 0.5 μL of the suspension was spotted onto the SERS substrate and spectra were collected after 60 minutes. SERS spectra were obtained with a laser power of ~15 mW at 785 nm with collection times of 10 s. The displayed spectra are representative of data collected form multiple spots on the substrate.

The main bands in both the SERS spectra arise from nucleic acids, surface proteins, amino acids and lipid components of the cell membrane. The spectra are similar looking with the main difference being the relative intensities of the bands at 658 cm$^{-1}$ (Guanine), 733 cm$^{-1}$ (Adenine) and 797 cm$^{-1}$. There is also a difference in the spectral region between 500 cm$^{-1}$ and 600 cm$^{-1}$. It is possible to calculate the band ratios of the Adenine and Guanine bands to discriminate between the two bacteria; while *E. Coli* has a A/G ratio of ~2.1, the ratio in the case of *S. Aureus* is ~8.5.

It should be noted that the Bacteria gave very good SERS response with the Ag nanorod substrate. Embodiments of the present disclosure are able to distinguish between *E. Coli* and *S. Aureus* based on at least the following: the ratio of the Adenine and Guanine band intensities, and A/G for *E. Coli* is ~2.1 while for *S. Aureus* ~8.5 (Based on ratio calculated for 6 different spectra on a single substrate) in the region between 500 cm$^{-1}$-600 cm$^{-1}$. The SERS bands due to surface protein secondary/tertiary structure between 1500-1700 cm$^{-1}$ are similar. The background signal from the substrate is also present in this region so there is some contribution. The *E. Coli* spectra look similar to what has been published in the literature. (+/− a couple of bands).

Therefore, at least the following is claimed:

1. A method of detecting at least one biomolecule in a sample, comprising:
   attaching at least one first biomolecule to an array of nanorods on a substrate, wherein a tilt angle (β) between an individual nanorod and the substrate surface is about 0° to about 90°;
   exposing the substrate including the first biomolecule to the sample containing at least one of a second biomolecule and a third biomolecule; and
   measuring a surface enhanced Raman spectroscopy (SERS) spectrum, wherein a SERS spectrum of the array of nanorods and the first biomolecule is detectably different than a SERS spectrum of the array of nanorods, the first biomolecule, and the second biomolecule and a SERS spectrum of the array of nanorods, the first biomolecule, and the third biomolecule, and wherein the SERS spectrum of the array of nanorods, the first biomolecule, and the second biomolecule is detectably different than the SERS spectrum of the array of nanorods, the first biomolecule, and the third biomolecule.

2. The method of claim 1, wherein the nanorods are selected from one of the following materials: a metal, a metal oxide, a metal nitride, a metal oxynitride, a polymer, a multicomponent material, and combinations thereof.

3. The method of claim 2, wherein the material is selected from one of the following: silver, nickel, aluminum, silicon, gold, platinum, palladium, titanium, cobalt, copper, zinc, oxides of each, nitrides of each, oxynitrides of each, carbides of each, and combinations thereof.

4. The method of claim 1, wherein the first biomolecule is selected from: a polynucleotide, a protein, a polypeptide, a glycoprotein, lipid, a carbohydrate, a fatty acid, a fatty ester, a macromolecular polypeptide complex, and combinations thereof.

5. The method of claim 1, wherein each of the second biomolecule and the third biomolecule are selected from: a polypeptide, protein, glycoprotein, nucleic acid, eukaryotic cell, prokaryotic cell, virus, bacterium, protozoa, apicomplexan, trematodes, nematodes, fungus, spore, carbohydrate, lipid, vitamin, and combinations thereof.

6. The method of claim 1, wherein the first biomolecule is an antibody of the second biomolecule and the third biomolecule.

7. The method of claim 1, wherein each of the second biomolecule and the third biomolecule are each a virus.

8. The method of claim 1, wherein each of the second biomolecule and the third biomolecule are a virus selected from: human immunodeficiency virus (HIV), Parainfluenza virus (PIV), adenovirus (Ad), rhinovirus, respiratory syncytial virus (RSV), and influenza virus.

9. The method of claim 1, wherein the second biomolecule is a first strand of a first virus and the third biomolecule is a second strand of the first virus.

10. The method of claim 1, wherein the second biomolecule is a first strand of an influenza virus and the third biomolecule is a second strand of the influenza virus.

11. The method of claim 1, wherein the second biomolecule is a first strand of a respiratory syncytial virus (RSV) virus and the third biomolecule is a second strand of the RSV virus.

12. The method of claim 1, wherein the sample is selected from: blood, saliva, tears, phlegm, sweat, urine, plasma, lymph, spinal fluid, cells, microorganisms, a combination thereof and aqueous dilutions thereof.

13. The method of claim 1, wherein the second biomolecule and the third biomolecule are each a bacterium.

14. A method of detecting at least one virus in a sample, comprising:
   exposing a substrate having an array of nanorods on the substrate to the sample including at least one of a first virus and a second virus, wherein a tilt angle (β) between an individual nanorod and the substrate surface is about 0° to about 90°; and
   measuring a surface enhanced Raman spectroscopy (SERS) spectrum, wherein a SERS spectrum of the array of nanorods and first virus is detectably different than a SERS spectrum of the array of nanorods and the second virus.

15. The method of claim 14, wherein the first virus and the second virus are two different types of viruses.

16. The method of claim 14, wherein the first virus and the second virus are the same type of virus, wherein the first virus corresponds to a first strand and the second virus corresponds to a second strand, wherein the first strand has a first measurable surface-enhanced Raman spectroscopic signature, wherein the second strand has a second measurable surface-enhanced Raman spectroscopic signature, and wherein the first measurable surface-enhanced Raman spectroscopic signature and the second measurable surface-enhanced Raman spectroscopic signature are distinguishable.

17. The method of claim 14, wherein the first virus and the second virus are the same type of virus, wherein the first virus corresponds to a first strand and the second virus corresponds to a second strand, and wherein the first strand and the second strand are different strands of the same type of virus.

18. The method of claim 17, wherein each of the first virus and the second virus are selected from: human immunodeficiency virus (HIV), Parainfluenza virus (PIV), adenovirus (Ad), rhinovirus, respiratory syncytial virus (RSV), and influenza virus.

19. The method of claim 17, wherein the first virus is a first strand of an influenza virus and the second virus is a second strand of the influenza virus.

20. The method of claim 17, wherein the first virus is a first strand of a respiratory syncytial virus (RSV) virus and the second virus is a second strand of the RSV virus.

21. The method of claim 14, wherein the array of nanorods has a first biomolecule disposed on each of the nanorods, and wherein the first biomolecule has an affinity for at least one of the first virus and the second virus.

22. The method of claim 1, wherein the array of nanorods includes nanorods having a length of about 10 to 10000 nanometers, and a diameter of about 50 to 150 nanometers.

23. The method of claim 1, wherein a distance between individual nanorods in the array is between about 10 nanometers to about 200 nanometers.

24. The method of claim 1, wherein the tilt angle (β) between an individual nanorod and the substrate surface is about 5° to about 20°.

25. The method of claim 1, wherein the tilt angle (β) between an individual nanorod and the substrate surface is about 25° to about 40°.

26. The method of claim 14, wherein the array of nanorods includes nanorods having a length of about 10 to 10000 nanometers, and a diameter of about 50 to 150 nanometers.

27. The method of claim 14, wherein a distance between individual nanorods in the array is between about 10 nanometers to about 200 nanometers.

28. The method of claim 14, wherein the tilt angle ($\beta$) between an individual nanorod and the substrate surface is about 5° to about 20°.

29. The method of claim 14, wherein the tilt angle ($\beta$) between an individual nanorod and the substrate surface is about 25° to about 40°.

* * * * *